(12) United States Patent
Miley et al.

(10) Patent No.: US 12,296,147 B2
(45) Date of Patent: May 13, 2025

(54) AUTOINJECTOR

(71) Applicant: SHL MEDICAL AG, Zug (CH)

(72) Inventors: Thad Miley, Boca Raton, FL (US); Dane Kris, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 798 days.

(21) Appl. No.: 17/294,237

(22) PCT Filed: Nov. 20, 2019

(86) PCT No.: PCT/EP2019/081918
§ 371 (c)(1),
(2) Date: May 14, 2021

(87) PCT Pub. No.: WO2020/120087
PCT Pub. Date: Jun. 18, 2020

(65) Prior Publication Data
US 2022/0016346 A1  Jan. 20, 2022

Related U.S. Application Data

(60) Provisional application No. 62/780,130, filed on Dec. 14, 2018.

(30) Foreign Application Priority Data

Jan. 23, 2019  (EP) .................................. 19153358

(51) Int. Cl.
*A61M 5/20* (2006.01)
*A61M 5/24* (2006.01)
(Continued)

(52) U.S. Cl.
CPC ........ *A61M 5/2033* (2013.01); *A61M 5/2466* (2013.01); *A61M 5/31505* (2013.01);
(Continued)

(58) Field of Classification Search
CPC .............. A61M 5/315; A61M 5/31505; A61M 5/31576; A61M 5/34; A61M 5/344;
(Continued)

(56) References Cited

U.S. PATENT DOCUMENTS

| 2013/0035644 A1* | 2/2013 | Bendek | A61M 5/2466 |
| | | | 604/192 |
| 2013/0131595 A1* | 5/2013 | Ekman | A61M 5/2033 |
| | | | 604/117 |

(Continued)

FOREIGN PATENT DOCUMENTS

| CN | 102264417 A | 11/2011 |
| CN | 102869399 B | 6/2015 |

(Continued)

OTHER PUBLICATIONS

International Search Report and Written Opinion for Int. App. No. PCT/EP2019/081918, mailed Dec. 18, 2019.

*Primary Examiner* — Phillip A Gray
*Assistant Examiner* — Forrest Blake Dipert
(74) *Attorney, Agent, or Firm* — McDonnell Boehnen Hulbert & Berghoff LLP

(57) ABSTRACT

A medicament delivery device is presented having a housing, a container assembly, a needle assembly and a driver assembly. The container assembly includes a medicament container having an interior containing a medicament. The needle assembly is connected to the container assembly and has a needle and an outer cap, wherein the outer cap is configured to be manually manipulated to move the needle toward the medicament container in order for a distal end of the needle to pierce a first seal and enter an interior of the medicament container. The driver assembly is disposed at a distal end of the medicament container and configured to be released and move the container assembly and the needle (Continued)

assembly toward the proximal end of the housing to an insertion position where a proximal end of the needle exits the housing.

17 Claims, 24 Drawing Sheets

(51) Int. Cl.
  *A61M 5/315* (2006.01)
  *A61M 5/32* (2006.01)
(52) U.S. Cl.
  CPC ...... *A61M 5/31576* (2013.01); *A61M 5/3202* (2013.01); *A61M 2005/2026* (2013.01); *A61M 2005/206* (2013.01); *A61M 2005/2086* (2013.01); *A61M 2005/2474* (2013.01); *A61M 2005/3247* (2013.01); *A61M 2005/3267* (2013.01)
(58) Field of Classification Search
  CPC ................ A61M 5/347; A61M 5/2033; A61M 5/31525; A61M 2005/206; A61M 2005/2026; A61M 2005/2086; A61M 2005/2474; A61M 2005/3247; A61M 2005/3267
  See application file for complete search history.

(56) References Cited

U.S. PATENT DOCUMENTS

| | | | |
|---|---|---|---|
| 2013/0190694 A1* | 7/2013 | Barrow-Williams | A61M 5/2033 604/221 |
| 2014/0343507 A1 | 11/2014 | Karlsson et al. | |
| 2015/0209517 A1 | 7/2015 | Brunnberg et al. | |
| 2015/0224259 A1 | 8/2015 | Giambattista et al. | |
| 2015/0314077 A1 | 11/2015 | Karlsson et al. | |
| 2017/0259002 A1 | 9/2017 | Laiosa et al. | |
| 2019/0328968 A1* | 10/2019 | Giambattista | A61M 5/315 |
| 2019/0365999 A1* | 12/2019 | Säll | A61M 5/3204 |

FOREIGN PATENT DOCUMENTS

| | | |
|---|---|---|
| EP | 0956058 B1 | 1/2003 |
| JP | 2011-524212 A | 9/2011 |
| JP | 2012-506745 A | 3/2012 |
| JP | 2015-500124 A | 1/2015 |
| WO | 2010/049239 A1 | 5/2010 |
| WO | 2013/089616 A1 | 6/2013 |
| WO | 2018136840 A1 | 7/2018 |

* cited by examiner

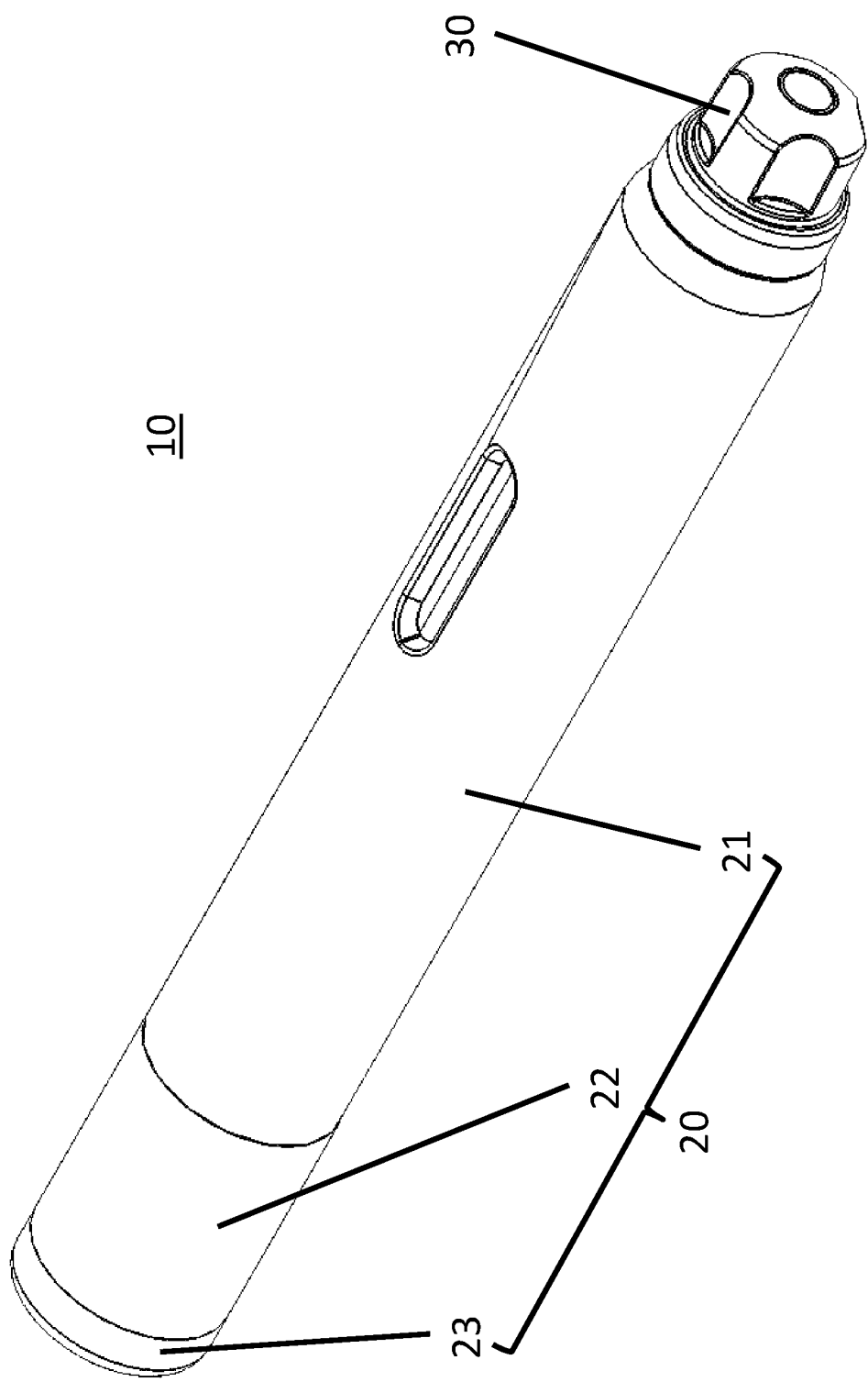

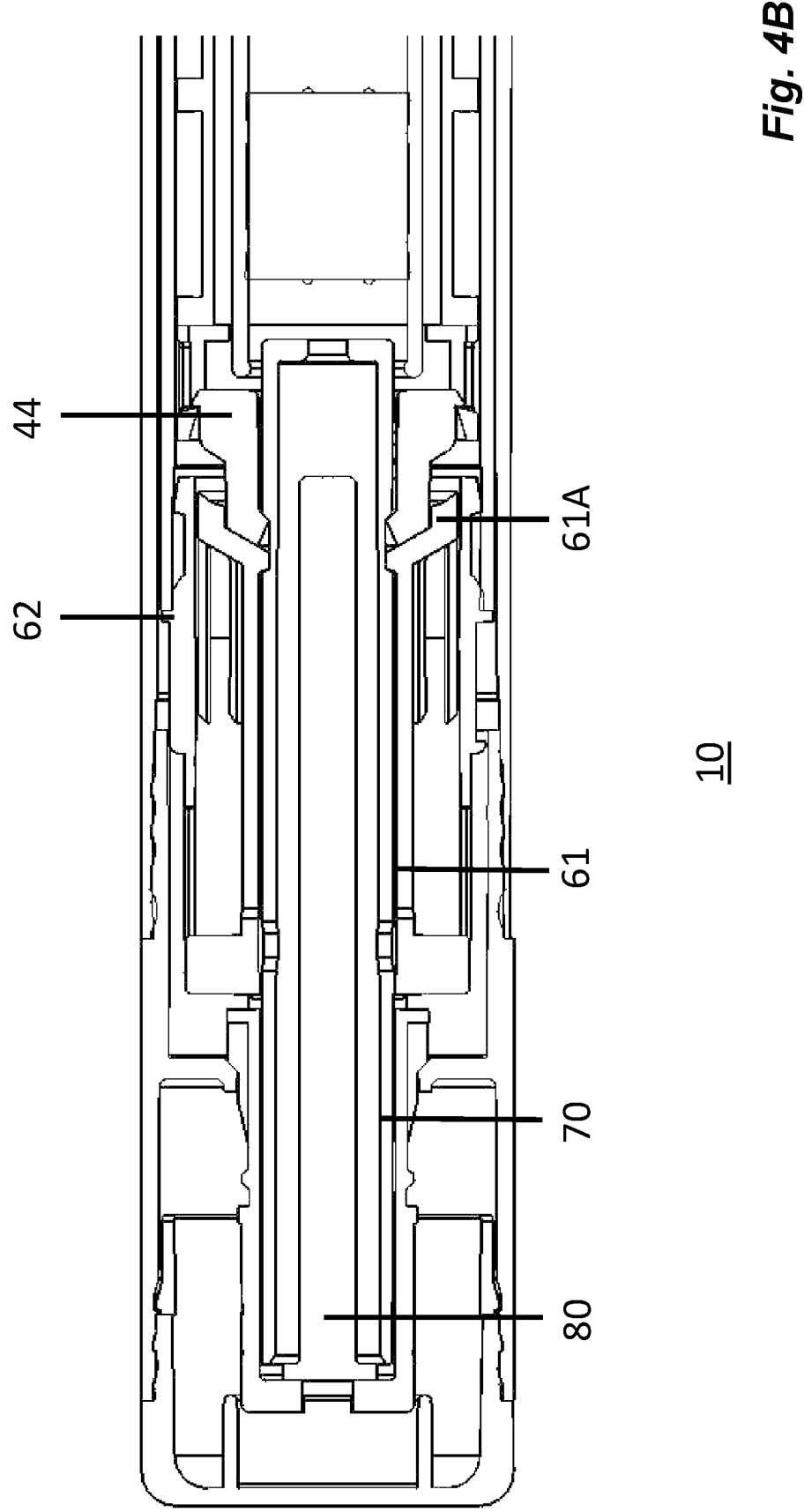

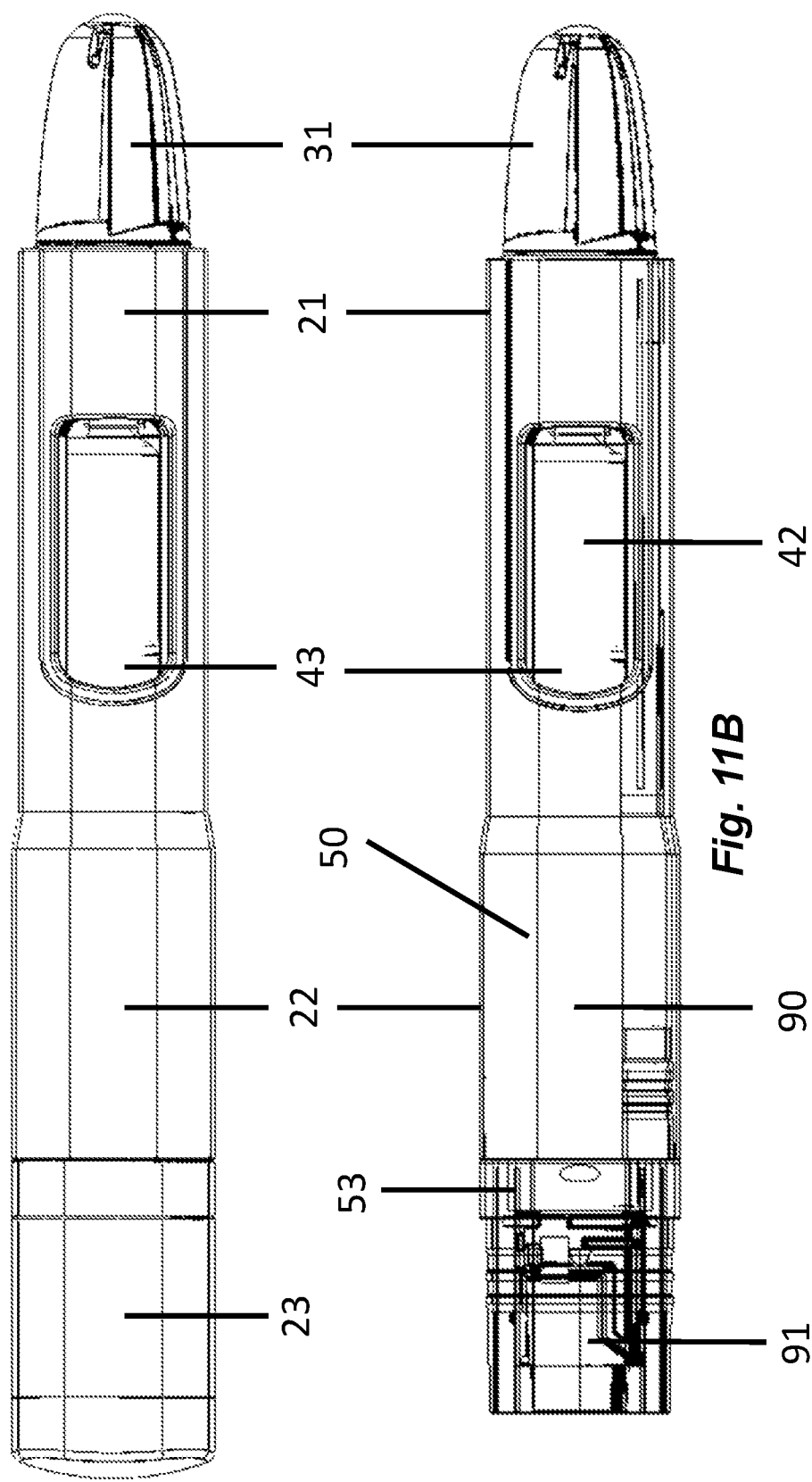

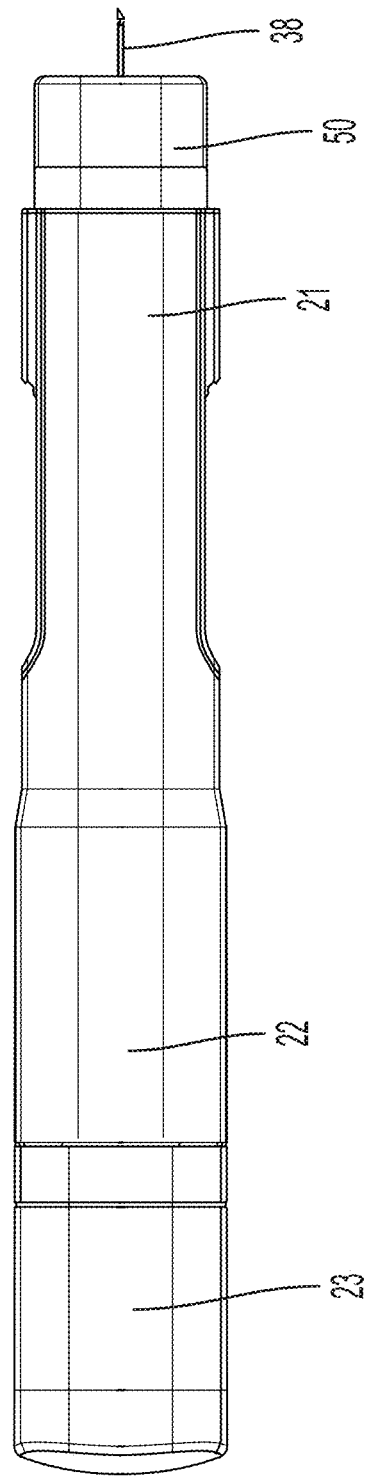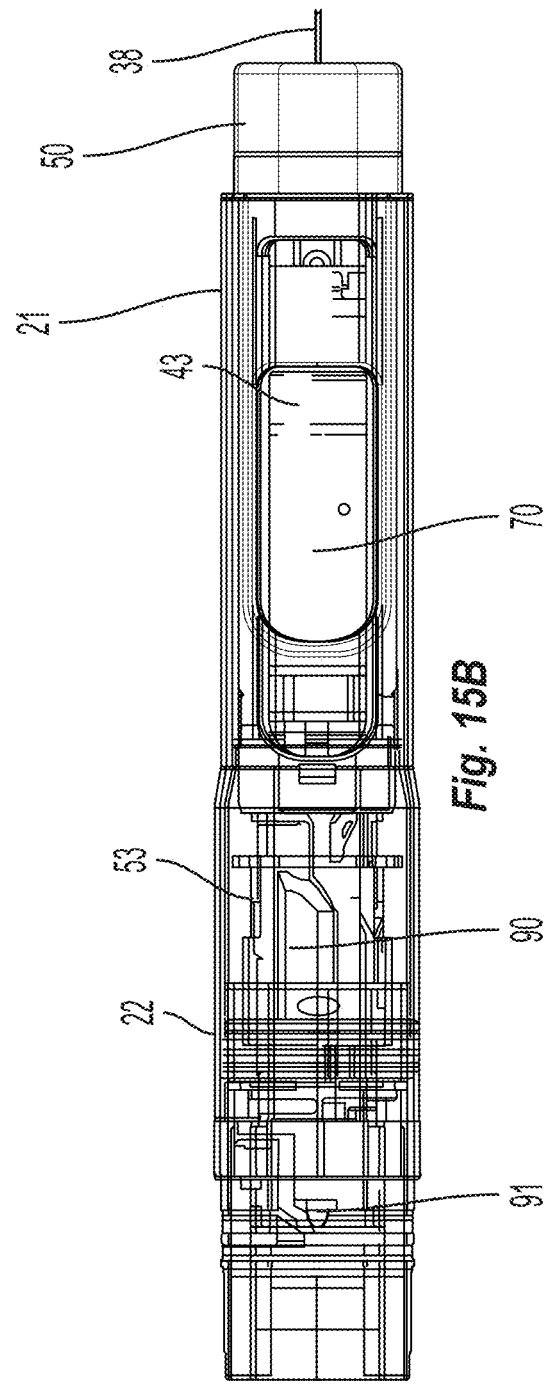

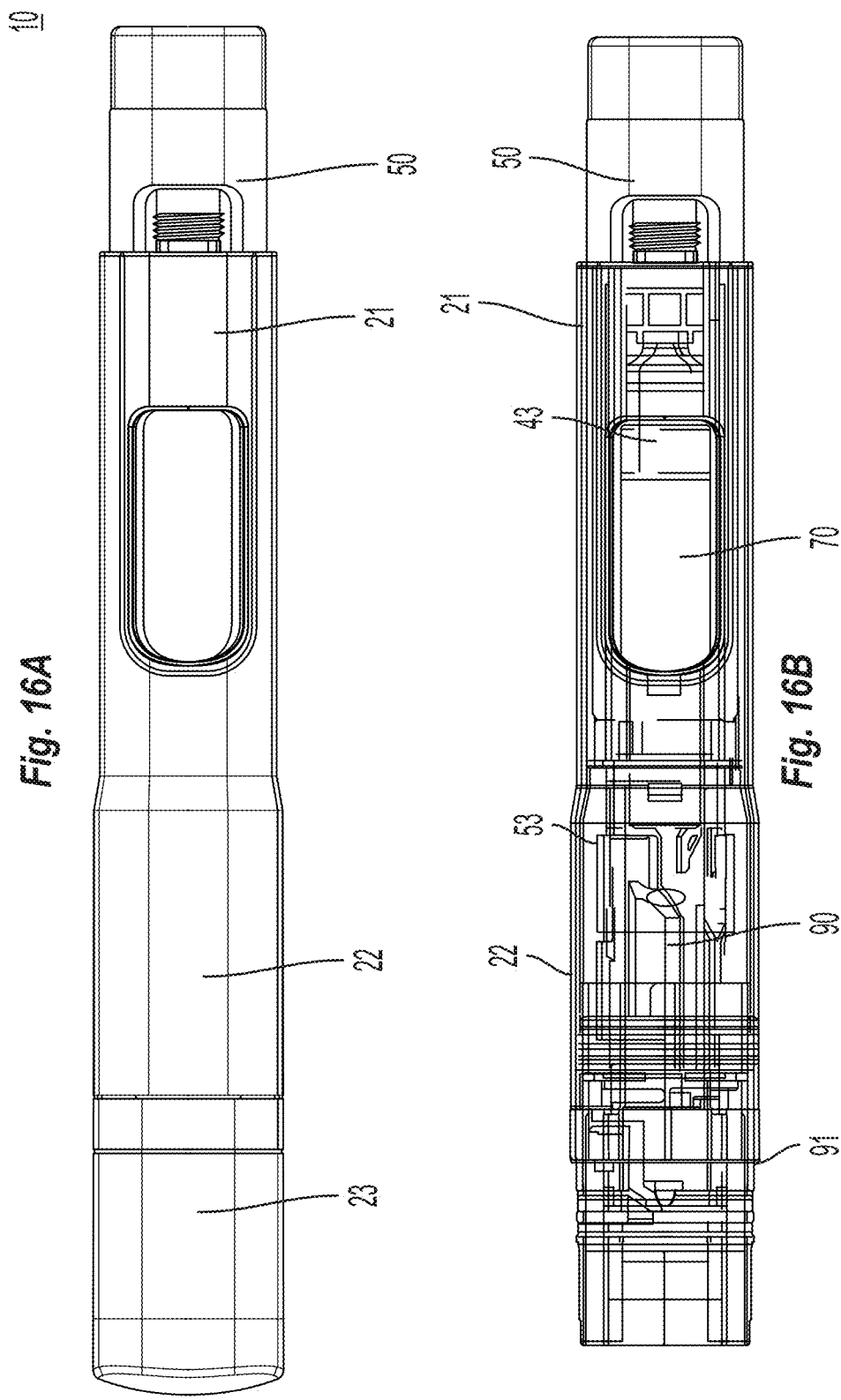

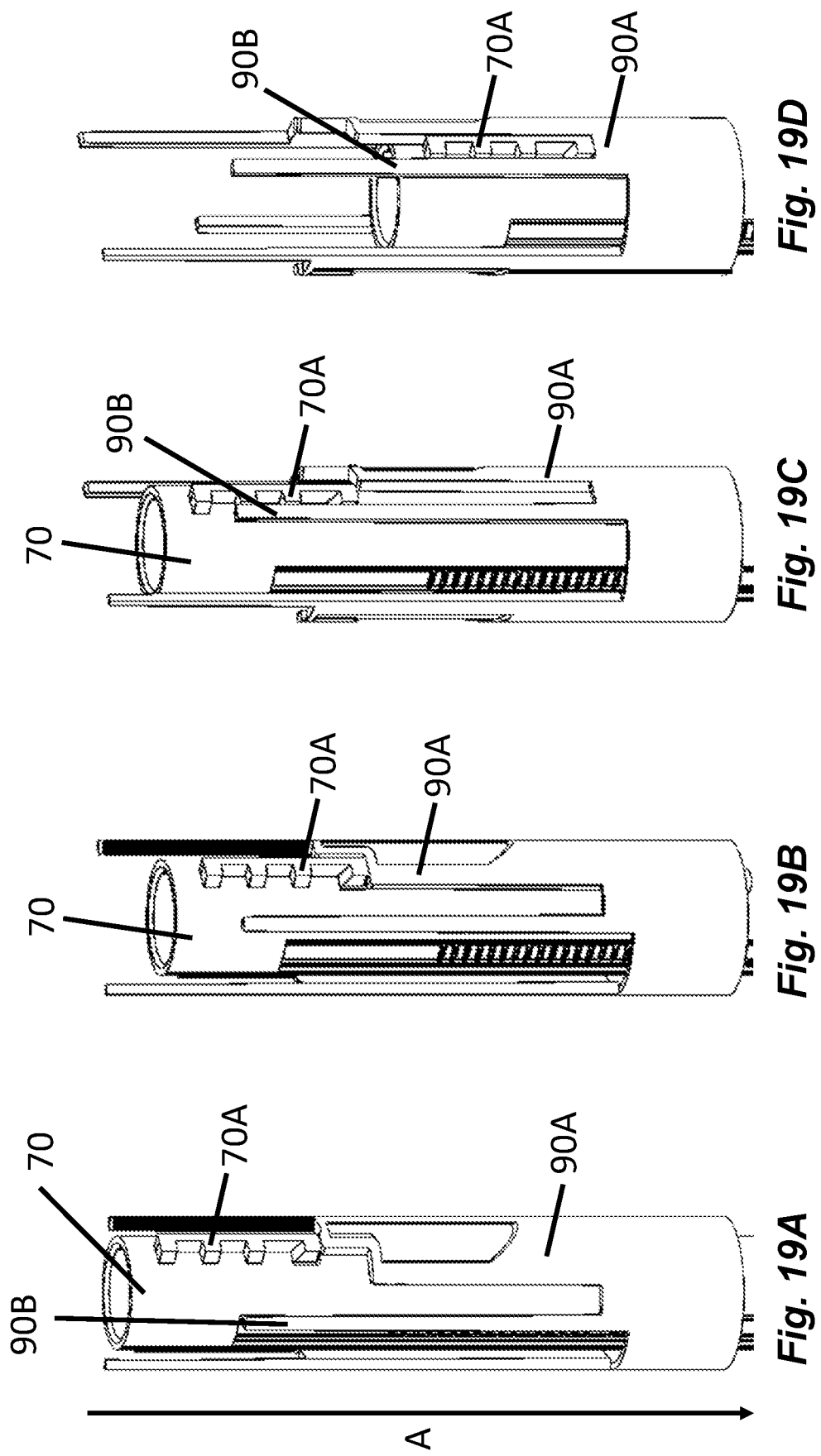

AUTOINJECTOR

CROSS REFERENCE TO RELATED APPLICATIONS

The present application is a U.S. National Phase Application pursuant to 35 U.S.C. § 371 of International Application No. PCT/EP2019/081918 filed Nov. 20, 2019, which claims priority to U.S. Provisional Patent Application No. 62/780,130 filed Dec. 14, 2018 and European Patent Application No. 19153358.7, filed Jan. 23, 2019. The entire disclosure contents of these applications are herewith incorporated by reference into the present application.

TECHNICAL FIELD

The present disclosure relates to a medicament injector and in particular to a medicament injector that requires manual attachment of needle to a medicament container and automatically performs the needle penetration at the injection site and the subsequent medicament injection into the injection site.

BACKGROUND

One type of drug delivery device known in the art is an autoinjector, which contains a medical, therapeutic, diagnostic, pharmaceutical or cosmetic compound (drug) before it is administered, and which is used to administer the compound through the skin of the patient via a hollow needle. Autoinjectors may be used by the patient themselves or by a different user, and are also used to administer drugs to animals. Injector devices are used to deliver a range of liquid medicaments.

Autoinjectors are typically used because they reduce the amount of training and effort needed by a user compared with that needed for a syringe, by automating either or both processes of inserting the needle into the patient and expelling the drug through the needle. They can also reduce the fear of injection by hiding the needle from the patient.

Correct use of an injector device by the patient is essential to ensure effective treatment of the respective medical condition. Such correct use includes ensuring the injection step occurs properly and the complete medicament dose is injected into the patient. It is advantageous to make the medicament delivery process straight-forward and intuitive for the patient to complete themselves. Incomplete or incorrect use of the injector device can result in ineffective treatment of the medical condition and potentially injury or discomfort to the patient. It is an object of the present disclosure to provide an injector device that addresses one or more of the problems mentioned above and to provide an improved injector device.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

In view of the foregoing, a general object of the present disclosure is to provide a needle shield remover for a cap of a medicament delivery device, which needle shield remover is easier to assemble.

These and other aspects of, and advantages with, the present disclosure will become apparent from the following detailed description of the present disclosure and from the accompanying drawings.

According to a main aspect of the disclosure it is characterized by a medicament delivery device, comprising a housing having a proximal end and a distal end; a movable container assembly disposed in the housing and including a medicament container having an interior containing a medicament, wherein the medicament container comprises a stopper and a first seal sealing the interior; a needle assembly connected to the movable container assembly and having a needle and an outer cap, wherein the outer cap is configured to be manually manipulated to move the needle toward the medicament container in order for a distal end of the needle to pierce the first seal and enter the interior; a driver assembly disposed at a distal end of the medicament container and configured to be released and move the container assembly and the needle assembly toward the proximal end of the housing to an insertion position where a proximal end of the needle exits the housing.

The medicament delivery device may further comprise an activator disposed in the housing and configured to engage the driver assembly, the activator being movable from a first activator position to a second activator position where the activator releases the driver assembly to move the container assembly and the needle assembly.

The medicament delivery device may further comprising an first resilient member configured to engage the activator or the driver assembly and moves the activator from the second activator position to a third activator position where the driver assembly abuts and prevents the activator from moving toward the distal end of the housing.

The driver assembly preferably include: a plunger rod configured to interact with the stopper in the medicament container; a first sleeve having at least one engagement portion configured to engage the plunger rod and prevent the plunger rod from moving; a second sleeve configured to engage the engagement portion and prevent the engagement portion from moving and disengaging the plunger rod; a second resilient member configured to engage the plunger rod and applying forces on the plunger rod in a proximal direction. The activator in the second activator position moves the second sleeve to disengage the engagement portion so that the engagement portion can move and disengage the plunger rod to release the resilient member to move the plunger rod which then engages the stopper to move the container assembly and the needle assembly toward the proximal end of the housing.

The second resilient member is configured to drive the plunger rod to push the stopper to reach a proximal end of the interior, the second resilient member then pushes the first sleeve toward the distal end of the housing to a position where the first sleeve abuts the second sleeve which abuts the activator and prevents the activator from moving toward the distal end of the housing.

The engagement portion is preferably radially flexible and positioned between the second sleeve and the plunger rod, the activator moving from the first activator position to the second activator position moves the second sleeve and allows the engagement portion to flex radially outward to disengage the plunger rod.

When the container assembly and the needle assembly are in the insertion position, the second resilient member pushes the plunger rod and the stopper to move the medicament through the distal end of the needle and then exits the needle through a proximal end of the needle. The plunger rod pushes the stopper to reach a proximal end of the interior, the second resilient member then pushes the first sleeve toward the distal end of the housing and creates an injection end signal when the first sleeve makes contact with the housing. On the other hand, the engagement portion is preferably radially flexible, the second sleeve is coupled with the activator, when the plunger rod pushes the stopper to reach a proximal end of the interior, the second resilient member then pushes the first sleeve toward the distal end of the housing for the engagement portion to flex radially inward to pass through the second sleeve and then flex radially outward to abut a distal portion of the obstruction portion and prevent the second sleeve and the activator from moving in a distal direction.

Further, the driver assembly may further include a guide rod disposed between the resilient member and the first sleeve, the guide rod is surrounded by the resilient member.

The needle assembly includes: a needle holder configured to engage and hold the needle; an inner cap configured to engage and rotate the needle holder; a retainer configured to be coupled with the container assembly and has a threaded portion threadedly engaged with the needle holder. The outer cap is configured to rotatably engage the inner cap and be manually rotated by a user to rotate the inner cap which in turn rotates the needle holder along the threaded portion and toward the medicament container in order for the distal end of the needle to pierce the seal and enter the interior.

The outer cap has a first coupler configured to couple with the inner cap so that the outer cap can remove the inner cap away from the proximal end of the medicament container when manually pulled by the user. The first seal is disposed on a proximal end of the medicament container, the needle assembly further includes a second seal positioned between the needle and the first seal, wherein the needle pierces the second seal and then the first seal when the needle holder is rotated along the threaded portion and toward the medicament container.

The needle assembly includes a clutch positioned between the outer cap and the inner cap and configured to rotatably engage the inner cap and the outer cap, the outer cap rotated in a first rotational direction rotates the clutch which in turn rotates the inner cap, the outer cap rotated in a second rotational direction does not engage the clutch and is prevented from rotating the clutch. The outer cap has a plurality of teeth disposed on an inner surface of the outer cap, the clutch has at least one radially flexible clutch arm configured to interact with the teeth, the tooth of the outer cap rotated in the first rotational direction engages the clutch arm to rotate the clutch, the tooth of the outer cap rotated in the second rotational direction pushes the clutch arm to flex radially inward and disengage the tooth.

The retainer has a second coupler configured to couple with the medicament container.

The container assembly includes a container carrier configured to accommodate the medicament carrier, wherein the released driver assembly moves both the medicament container and the container carrier toward the proximal end of the housing to the insertion position where the housing engages the container carrier and stops a movement of the container assembly. The container carrier generates an insertion end signal when the container carrier reaches the insertion position and makes contact with the housing.

The medicament delivery device may further comprise a third coupler coupling with the container assembly and the driver assembly, the released driver assembly moves the third coupler which in turn moves the container assembly and the needle assembly toward the insertion position, the driver assembly then decouples from the third coupler and then pushes the stopper to move the medicament through the distal end of the needle and then exits the needle through the proximal end of the needle.

The feature of moving both the container assembly and needle assembly toward the proximal end of the housing is advantageous as it ensures that needle penetration and medicament injection occur automatically and in sequence. This saves the user the trouble of having to perform the needle penetration and medicament injection by himself/ herself which may cause discomfort and mental stress.

Also, the feature of requiring user to manually manipulating the outer cap of needle assembly to move the needle to pierce the first seal of the medicament container is advantageous as it ensures the sterility of both the needle and medicament container before usage.

BRIEF DESCRIPTION OF DRAWINGS

In the following detailed description of the present disclosure, reference will be made to the accompanying drawings, of which FIG. 1A is a perspective view of the example autoinjector according to a first embodiment of the present disclosure.

FIG. 4B is a cross-sectional view of the rear portion of the autoinjector after the removal of caps of the needle assembly.

FIGS. 11A and 11B are perspective views of the example autoinjector according to a second embodiment before the outer cap is removed.

FIGS. 15A and 15B are perspective views of the example autoinjector according to a second embodiment at the end of medicament injection.

FIGS. 16A and 16B are perspective views of the example autoinjector according to a second embodiment after the autoinjector is removed from the injection site.

FIGS. 19A, 19B, 19C and 19D are perspective views of the plunger rod interacting with the inner surface of the rotator.

DETAILED DESCRIPTION

Figure 1B:
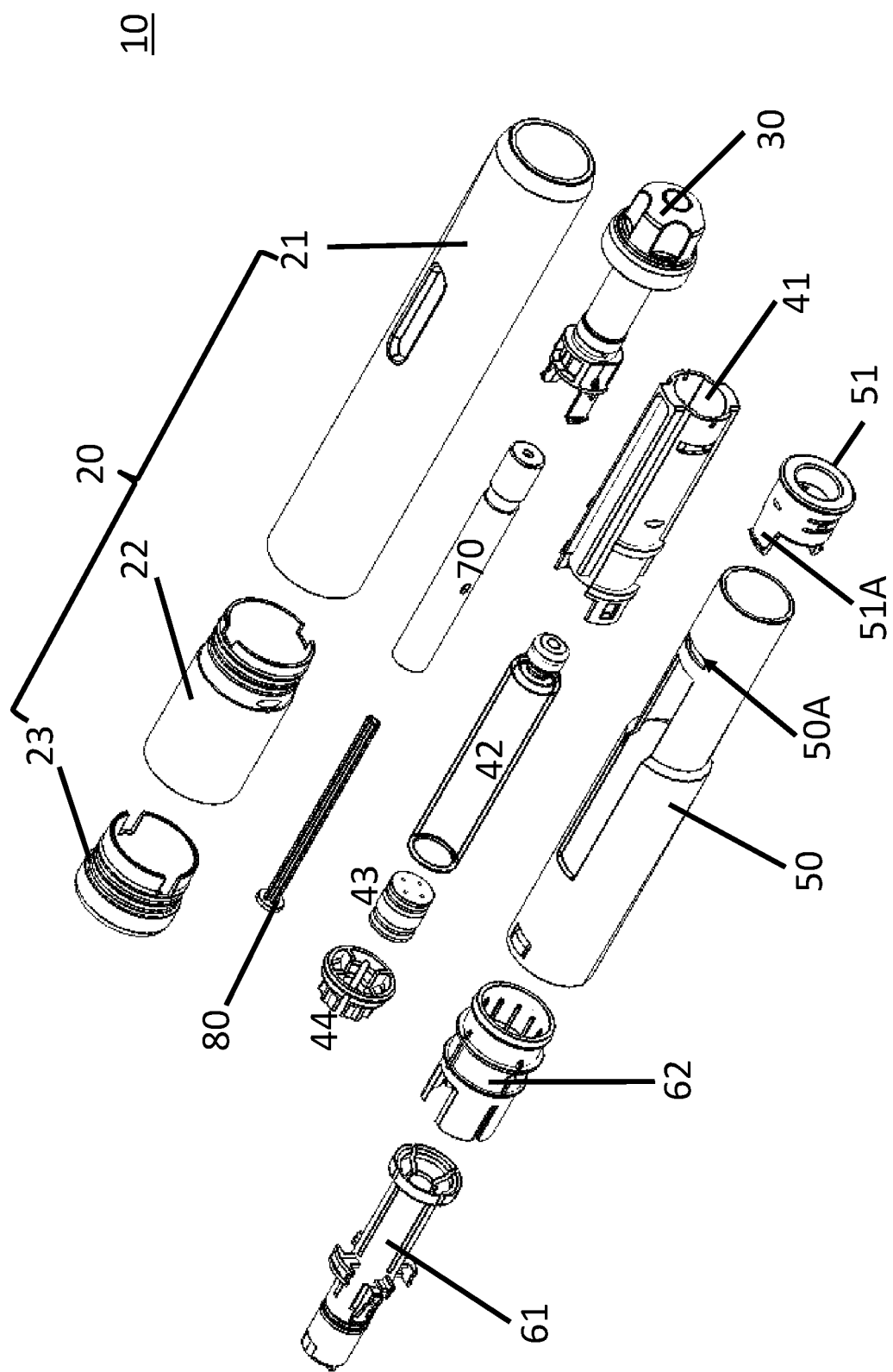
FIG. 1B is an exploded view of the example autoinjector according to a first embodiment of the present disclosure.

FIG. 1A shows a perspective view of the example autoinjector 10 according to a first embodiment of the present disclosure. As illustrated, the autoinjector 10 includes a housing 20 and a needle assembly 30 disposed at the proximal end of the housing 20. In the present embodiment, the housing 20 includes a front shell 21, a rear shell 22, and a rear shell cap 23 each having threads designed to allow coupling between them through rotation. However, in other embodiments, the components of the housing 20 can have other configurations known in the art such as cams and grooves that allow the manufacturers to couple them together.

FIG. 1B shows an exploded view of an example autoinjector 10 according to a first embodiment of the present disclosure. The autoinjector 10 comprises the housing 20, the needle assembly 30, a container carrier 41, a medicament container 42, a stopper 43, a needle cover 50, a needle cover front 51, a first sleeve 61, a second sleeve 62, a plunger rod 70, and a guide rod 80. The purpose of each of said components and the interaction between them will be explained in the following paragraphs. Further, the autoinjector 10 includes a plurality of resilient members (not illustrated) such as springs configured to push certain components in a proximal or distal direction. The locations of the resilient members and their interaction with the rest of the components illustrated in FIG. 1B will be explained in the following paragraphs.

Figure 2A:
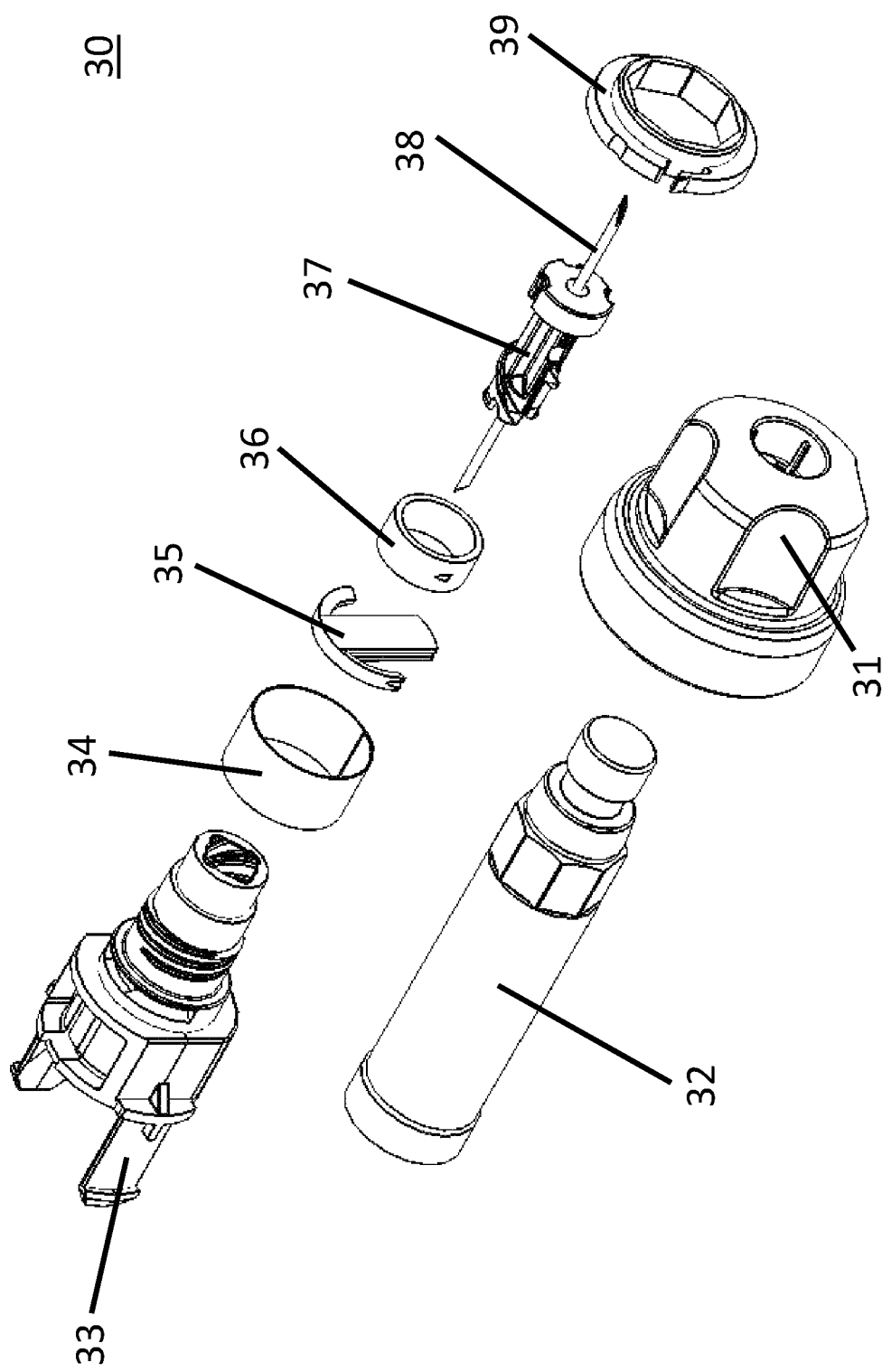
FIG. 2A is an exploded view of the needle assembly according to a first embodiment of the present disclosure.

FIG. 2A shows an exploded view of the needle assembly 30 according to a first embodiment of the present disclosure. The needle assembly 30 includes an outer cap 31, an inner cap 32, a retainer 33, a first sealing member 34, a second sealing member 35, a third sealing member 36, a needle holder 37, a needle 38 held by the needle holder 37, and a clutch 39. The purpose of the needle assembly 30 is to cover the proximal end of the autoinjector 10 and allows the user to manually move the needle 38 by rotating the caps 31, 32 to penetrate the sealing on the medicament container 42 and enter its interior in order to gain access to the medicament within. The user then can remove the caps 31, 32 by pulling them away from the housing 20. The processes of moving the needle 38 to enter the interior of medicament container 42 and removing the caps 31, 32 will be explained in the following paragraphs. Also, the inner cap 32, retainer 34, first sealing member 35, third sealing member 37, needle holder 38, and needle 38 and the interaction between these components have been disclosed in U.S. Patent Publication US2015314077A1 which is hereby incorporated by reference.

Figure 2B:
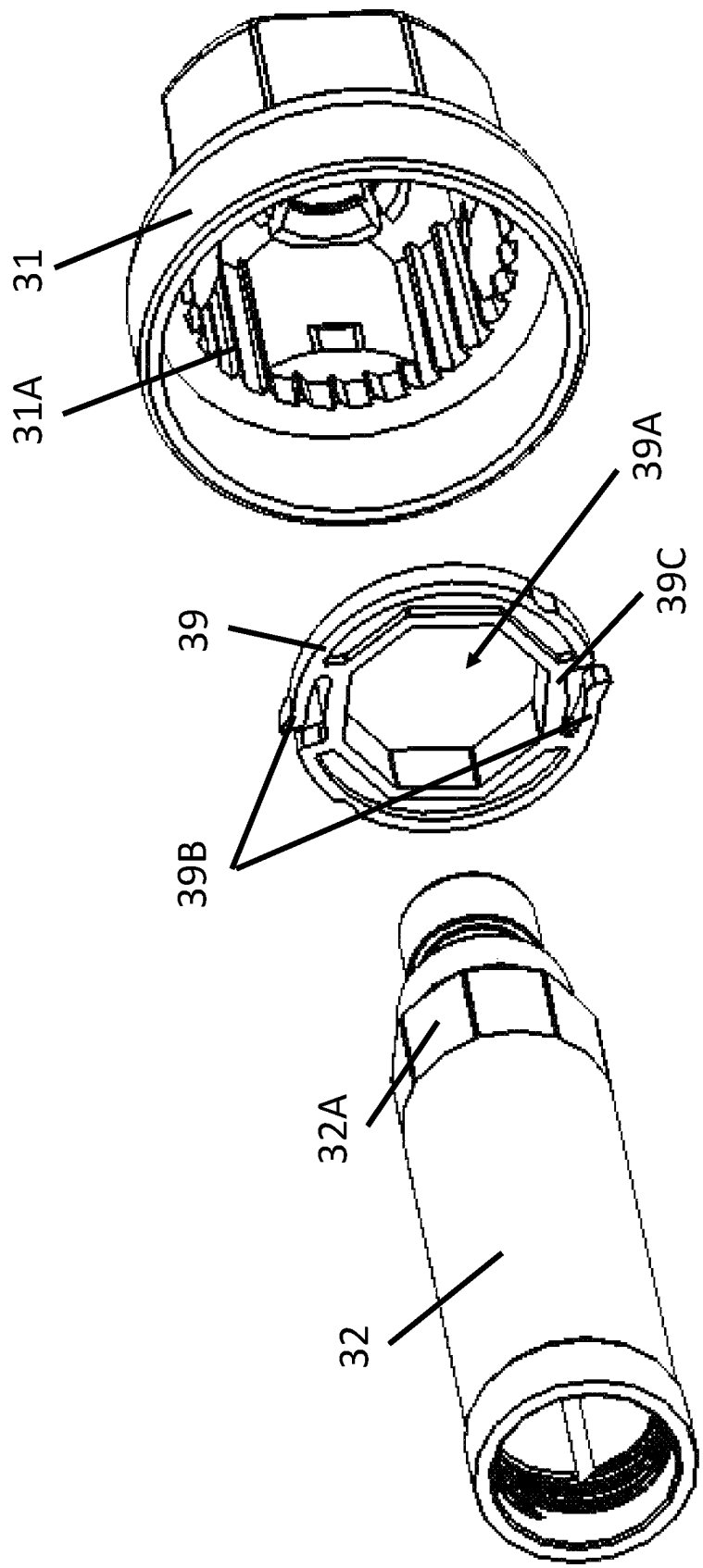
FIG. 2B is a perspective view of the outer cap, inner cap, and clutch according to a first embodiment of the present disclosure.

FIG. 2B is a perspective view of the outer cap 31, inner cap 32, and clutch 39 according to a first embodiment of the present disclosure. As illustrated, the inner cap 32 has a coupling portion 32A configured to couple with the clutch 39. The clutch 39 has an opening 39A whose shape and dimension correspond to those of the coupling portion 32A so that it can fit inside the opening 39A. On the other hand, the outer cap 31 includes a plurality of teeth 31A disposed on the inner surface of the outer cap 31 and configured to interact with the clutch 39. The clutch 39 includes a pair of clutch arms 39B configured to interact with said teeth 31A and an inner frame 39C connected to the clutch arms 39B. In this embodiment, the clutch arms 39B are radially flexible capable of flexing radially inward or outward depending on the direction of the forces exerted thereon.

When the user rotates the outer cap 31 in a counter-clockwise direction (looking from outer cap 31 toward the inner cap 32), the teeth 31A engages the end portion of the clutch arms 39B to push them to rotate the clutch 39 in a counter-clockwise direction. Since the opening 39A of the clutch 39 and the coupling portion 32A have corresponding shape, the counter-clockwise rotation of the clutch 39 allows the inner frame 39C to engage the coupling portion 32A and rotate the inner cap 32 in the counter-clockwise direction. On the other hand, if the user rotates the outer cap 31 in a clockwise direction (looking from outer cap 31 toward the inner cap 32), the teeth 31A presses on the clutch arms 39B radially inward to subsequently disengage the teeth 31A. The clutch arm 39B then flex radially outward to engage another tooth 31A but is then pressed radially inward again. The result is that the teeth 31A can never engage the clutch arms 39B to rotate the clutch 39 and the inner cap 32, as long as the outer cap 31 rotates in a clockwise direction.

Figure 2C:
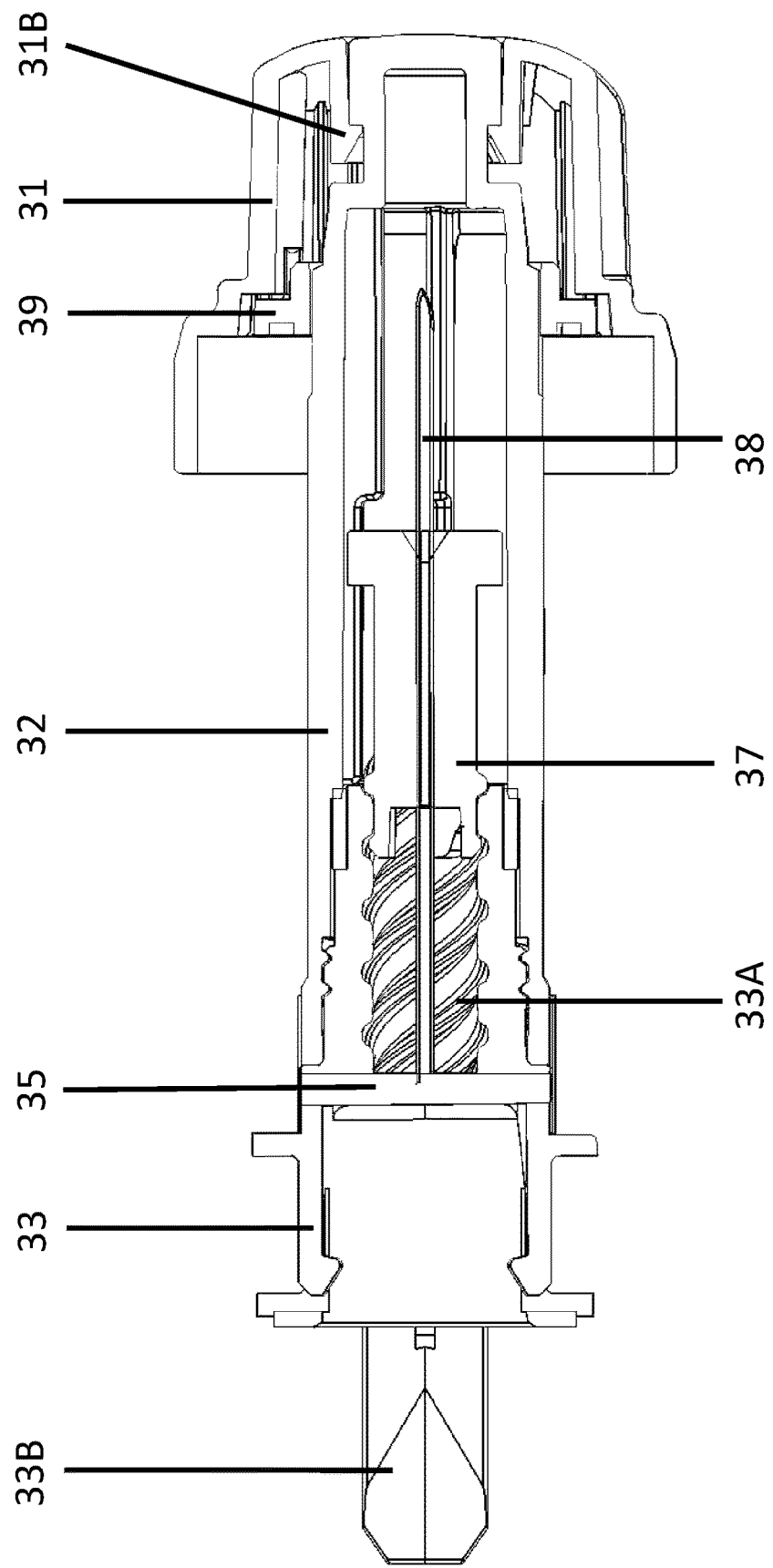
FIG. 2C is a cross-sectional view of the needle assembly according to a first embodiment of the present disclosure.

FIG. 2C shows a cross-sectional view of the needle assembly 30 according to a first embodiment of the present disclosure. As discussed above, the user rotates the outer cap 31 in a counter-clockwise direction (looking from outer cap 31 toward the inner cap 32) which in turn rotates the clutch 39 and then the inner cap 32 in the counter-clockwise direction. As described in the U.S. Patent Publication US2015314077A1, the inner cap 32 then rotates the needle holder 37 to interact with and travel along the threaded portion 33A of the retainer 33. The result is that the distal end of the needle 38 will penetrate the second sealing member 35 and then the sealing of the medicament container 42 (illustrated in FIG. 4).

As illustrated in FIG. 2C, the outer cap 31 has a coupling hook 31B configured to couple with the proximal end portion of the inner cap 32. Thus, the user can remove the caps 31, 32 by pulling the outer cap 31 away from the autoinjector 10. Also, as discussed above, the coupling portion 32A of the inner cap 32 is tightly fitted in the opening 39A of the clutch 39A. This creates a gripping forces for the inner cap 32 to move together with the clutch 39 when it's being pulled away by the outer cap 31. Accordingly, the removal of the outer cap 31 also results in the removal of both the inner cap 32 and the clutch 39. In addition, the retainer 33 includes a carrier coupling portion 33B configured to couple with the container carrier 41 so that a first resilient member can move the container carrier 41, the container carrier, medicament container 42, and the needle assembly 30 (less caps 31, 32 and clutch 39) all in the proximal direction.

Figure 3:
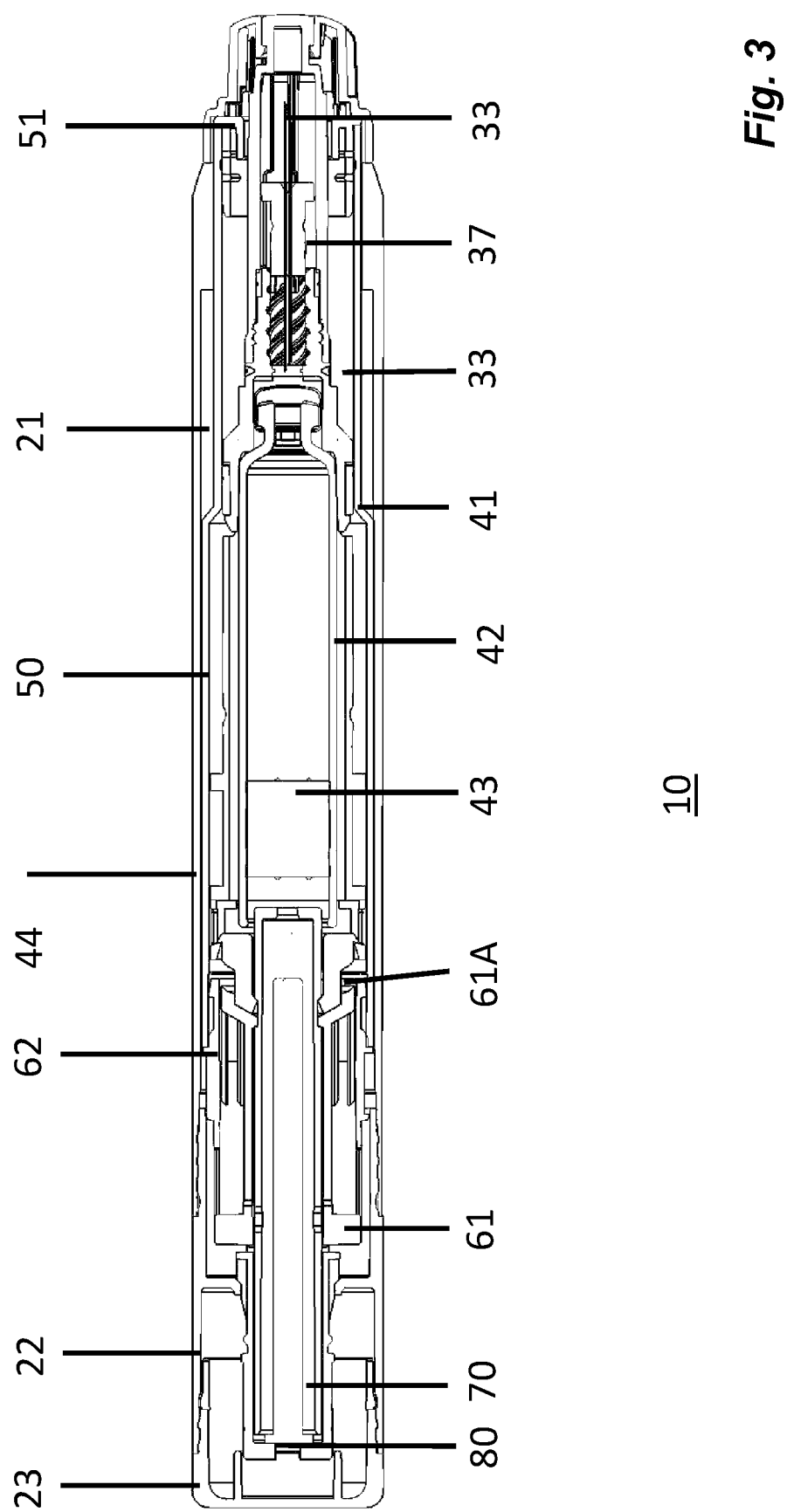
FIG. 3 is a cross-sectional view of the example autoinjector before the removal of caps of the needle assembly.

FIG. 3 shows a cross-sectional view of the example autoinjector 10 before the removal of the outer cap 31, inner cap 32 and clutch 39 and the penetration of the second sealing member 35 and that of the medicament container 42 by the needle 38.

Figure 4A:
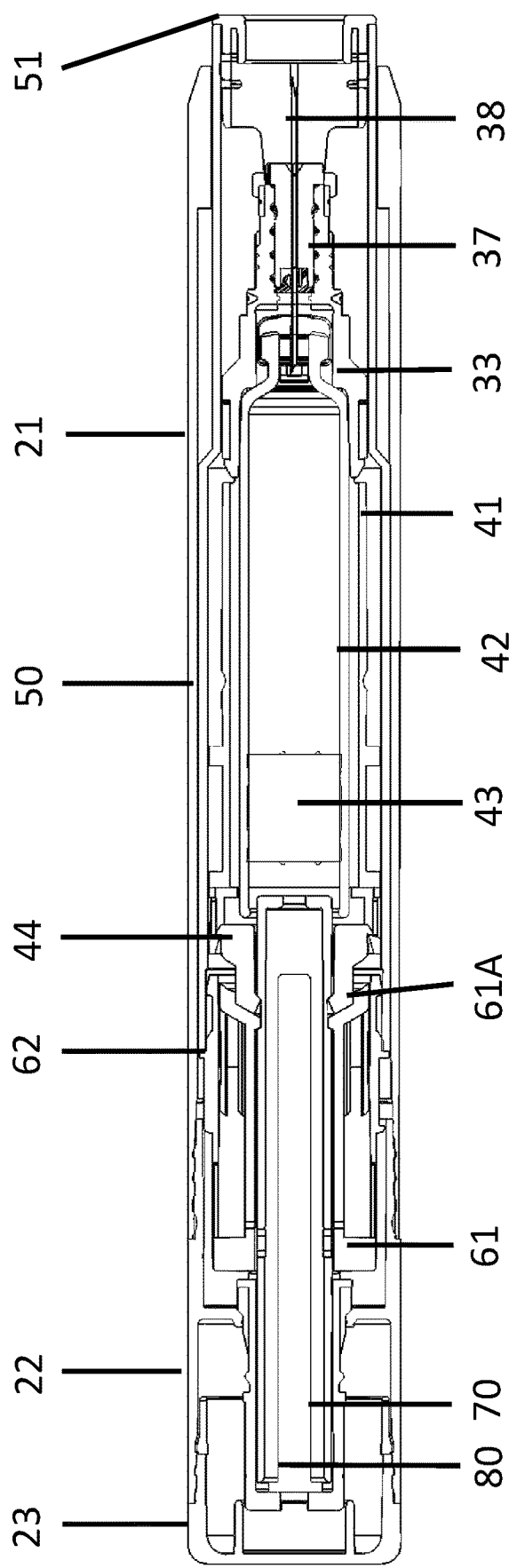
FIG. 4A is a cross-sectional view of the example autoinjector after the removal of caps of the needle assembly.

FIG. 4A shows a cross-sectional view of the example autoinjector 10 after the removal of the outer cap 31, inner cap 32 and clutch 39. The housing 20 that includes the front shell 21, rear shell 22, and rear shell cap 23 are coupled to enclose essentially the rest of the components of the autoinjector 10, except for the needle cover front 51 and proximal end of needle cover 50 protruding outside the housing 20. The needle cover front 51 is coupled with the needle cover 50 and is configured to make contact with an injection site (such as the user's arm) when the user is ready for the subsequent needle penetration and medicament injection. As illustrated in FIG. 1B, the needle cover front 51 has a pair of needle cover couplers 51A at its distal end. On the other hand, the needle cover 50 has a pair of openings 50A corresponding to the needle cover couplers 51A. The needle cover couplers 51A will flex radially inward when the needle cover front 51 is fitted in the proximal opening of the needle cover 50 and then flex radially outward to couple with the openings 50A in order to secure the needle cover 50 and needle cover front 51 together. Other forms of attachment method can also be used to couple the needle cover 50 and needle cover front 51. The needle cover 50 and needle cover 51 can also be made into an integral piece.

The container assembly that includes the container carrier 41, medicament container 42, stopper 43, and container carrier holder 44 is disposed within the confine of the needle cover 50. The medicament container 42 contains medicament to be injected into the injection site after needle penetration, wherein the stopper 43 maintains a liquid-tight sealing with the inner surface of medicament container 43 to make sure that medicament does not escape through the distal opening of the medicament container 42. On the other hand, the needle 38 is located at the proximal end of the interior of medicament container 42. The medicament is contained inside the medicament container 42 as it takes additional forces from the stopper 43 to push the medicament through the needle 38. Since the plunger rod 70 has not been released yet, the stopper 43 is stationary and thus the medicament also remains stationary within the medicament container 42.

The container carrier 41 is configured to enclose the medicament container 42 and interact with the front shell 21 during needle penetration while being moved toward the proximal end of the autoinjector 10. The interaction between the container carrier 41 and the front shell 21 during needle penetration will be explained later in the paragraphs below.

FIG. 4B is a cross-sectional view of the rear portion of the autoinjector after the removal of caps of the needle assembly. Firstly, a first resilient member (not illustrated) such as spring is disposed inside the plunger rod 70, wherein the guide rod 80 passes through the first resilient member to make sure that the first resilient member extends properly when released. The first resilient member, once released, will decompress to move the plunger rod 70 in the proximal direction and the guide rod 80 in the distal direction.

As illustrated in FIGS. 1B and 4B, a section of the plunger rod 70 is carved out to make a circular groove around the plunger rod 70. On the other hand, the first sleeve 61 has a pair of engagement portions 61A with protrusions that extend into the groove to engage the plunger rod 70. The first resilient member inside the plunger rod 70 is configured to push the plunger rod 70 in the proximal direction which then pushes the engagement portions 61A to flex radially outward. However, the second sleeve 62 is disposed between the housing 20 and the engagement 61A and it prevents the engagement portions 61A from flexing radially outward. Thus, the engagement portion 61A is forced to remain engaged with the plunger rod 70 and in the process hold the plunger rod 70 in place, despite the force from the first resilient member on the plunger rod 70 in the proximal direction. The container carrier holder 44 is also coupled with the groove on the plunger rod 70 and the interaction between the container carrier holder 44 and the plunger rod 70 will be explained later in the paragraphs below.

Figure 5:
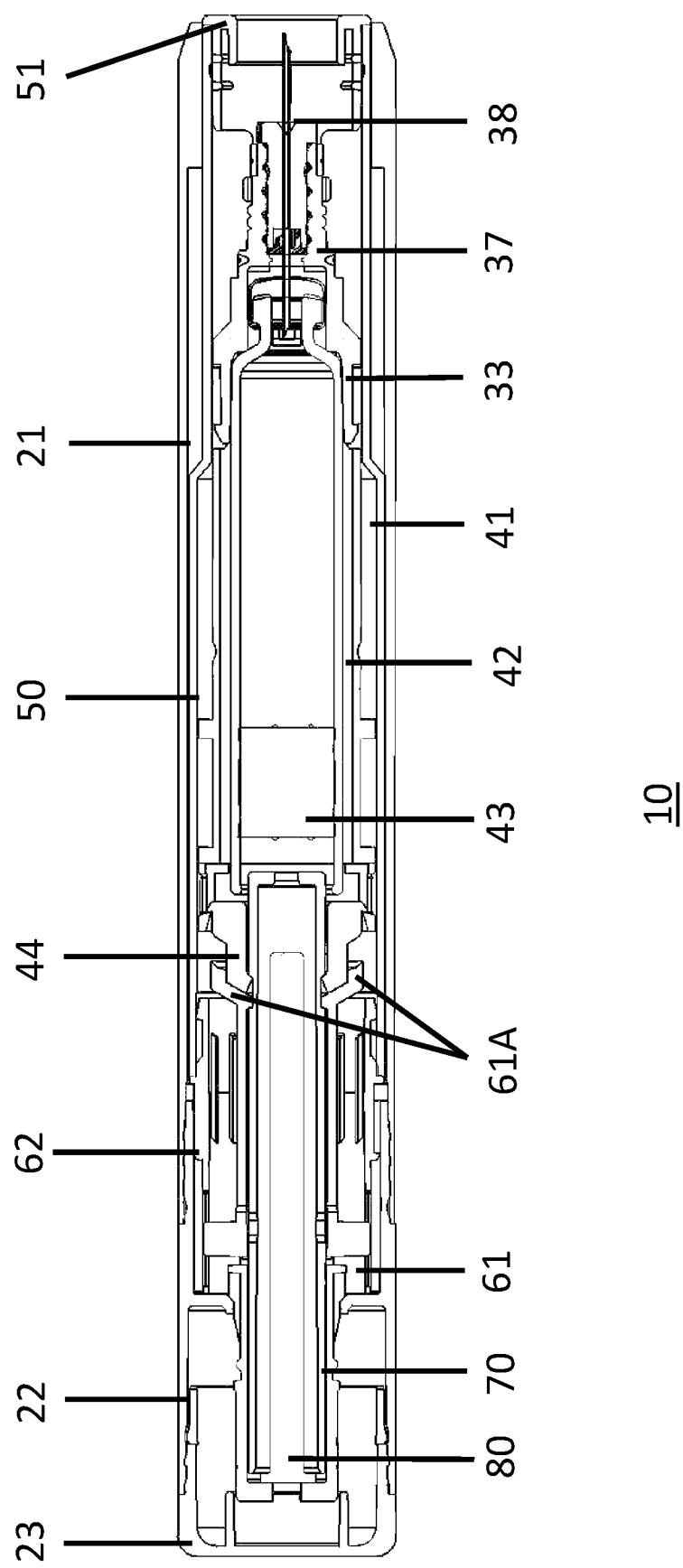
FIG. 5 is a cross-sectional view of the example autoinjector when the needle cover is pressed against injection site.

FIG. 5 is a cross-sectional view of the example autoinjector when the needle cover 50 is pressed against the injection site. The needle cover 50, when pressed against the injection site, is moved in the distal direction and its distal end will engage the second sleeve 62 to also move the second sleeve 62 in the distal direction. As illustrated in FIG. 5, the second sleeve 62 is no longer located between the housing 20 and the engagement portion 61A. Thus, the plunger rod 70 driven by the first resilient member can push the engagement portion 61A to flex radially outward and then be moved in the proximal direction. This is the beginning of needle penetration when the plunger rod 70 pushes the stopper 43 which then pushes the medicament to bring the rest of the container assembly (includes a container carrier 41, a medicament container 42, and container carrier holder 44) in the proximal direction in order for the needle 38 to protrude outside the housing 20 and penetrate the injection site.

Figure 6A:
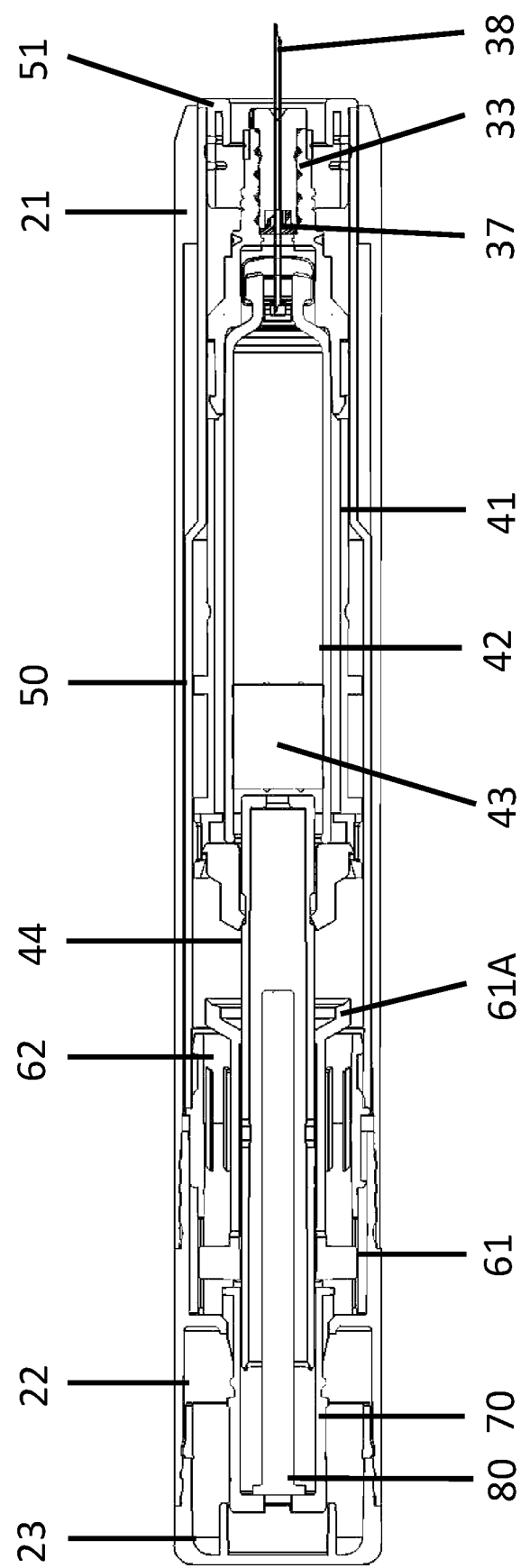
FIG. 6A is a cross-sectional view of the example autoinjector when the needle is fully extended outside the housing to penetrate the injection site.

FIG. 6A is a cross-sectional view of the example autoinjector when the needle 38 is fully extended outside the housing to penetrate the injection site. This configuration of the autoinjector 10 occurs after the first resilient member inside the plunger rod 70 is released to move the plunger rod 70 in the proximal direction. The engagement portion 61A of first sleeve 61 no longer engages the circular groove on the plunger rod 70. Instead, the container carrier holder 44 is the only component that engages the circular groove on the plunger rod 70. On the other hand, the container carrier holder 44 is also coupled with the container carrier 41. The engagement between the container carrier holder 44 and plunger rod 70 allows the plunger rod 70 to move the container carrier holder 44, container carrier 41, medicament container 42, and the rest of the needle assembly 30 in the proximal direction. Eventually, the container carrier 41 abuts the inner surface of housing 20 which then prevents the plunger rod 70 from moving the container carrier 41 any further in the proximal direction.

Figure 6B:
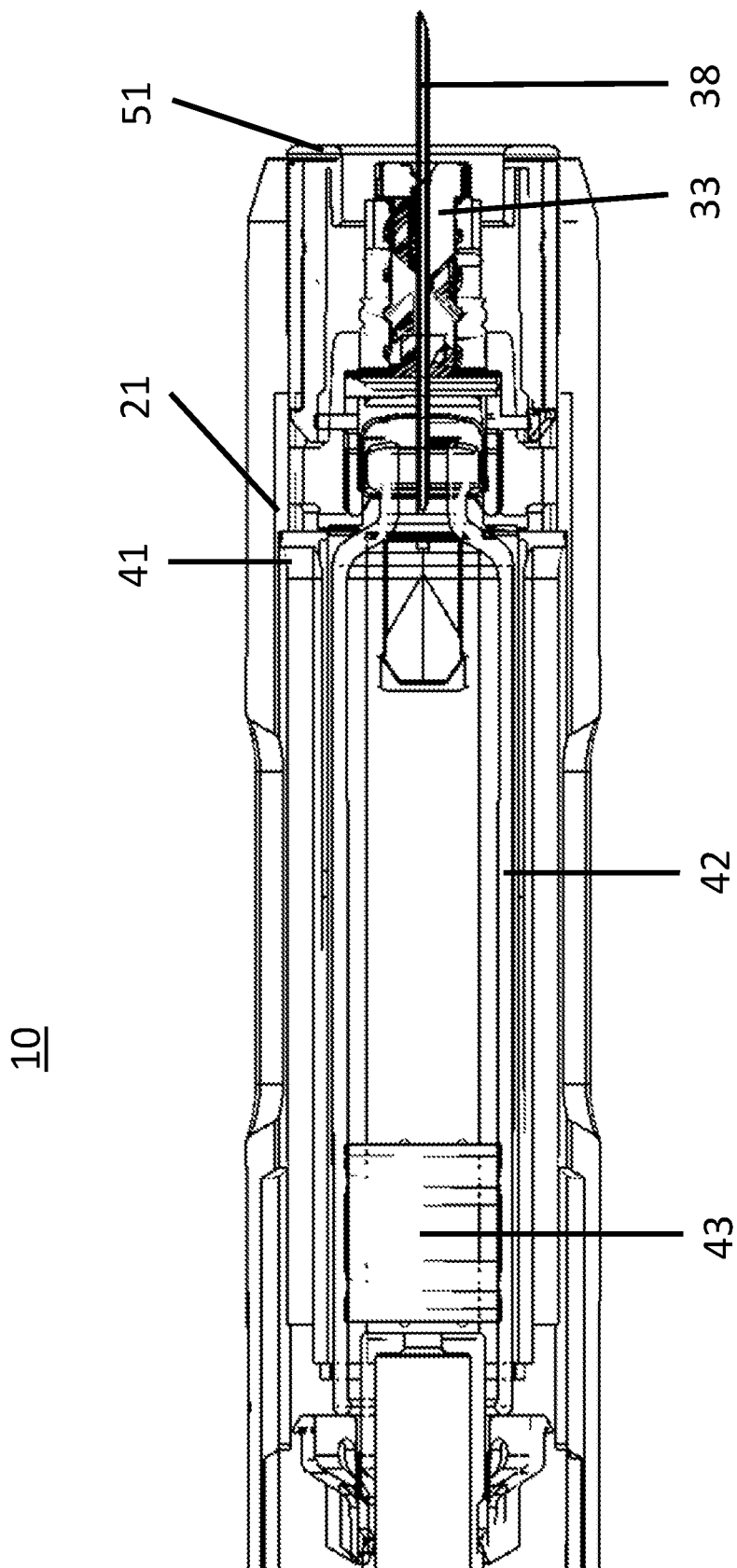
FIG. 6B is another cross-sectional view of the example autoinjector when the needle is fully extended outside the housing to penetrate the injection site.

FIG. 6B is another cross-sectional view of the front portion of the autoinjector 10 when the needle 38 is fully extended outside the housing to penetrate the injection site. As illustrated, the proximal end of the container carrier 41 abuts the inner surface of the front shell 21. This engagement prevents the plunger rod 70 from moving the container carrier holder 44, container carrier 41, medicament container 42, and the rest of the needle assembly 30 any further. Thus, the needle 38 has reached its furthest distance outside the housing 20 and needle cover front 51. On the other hand, the first resilient member inside the plunger rod 70 is still pushing the plunger rod 70 in the proximal direction. This results in the container carrier holder 44 disengaging the circular groove on the plunger rod 70 in order for the plunger rod 70 to engage the stopper 43 and move the stopper 43 further in the proximal direction. This marks the end of the needle penetration of the autoinjector and the beginning of the medicament injection that propels the medicament through the needle 38 to enter the injection site.

Figure 7:
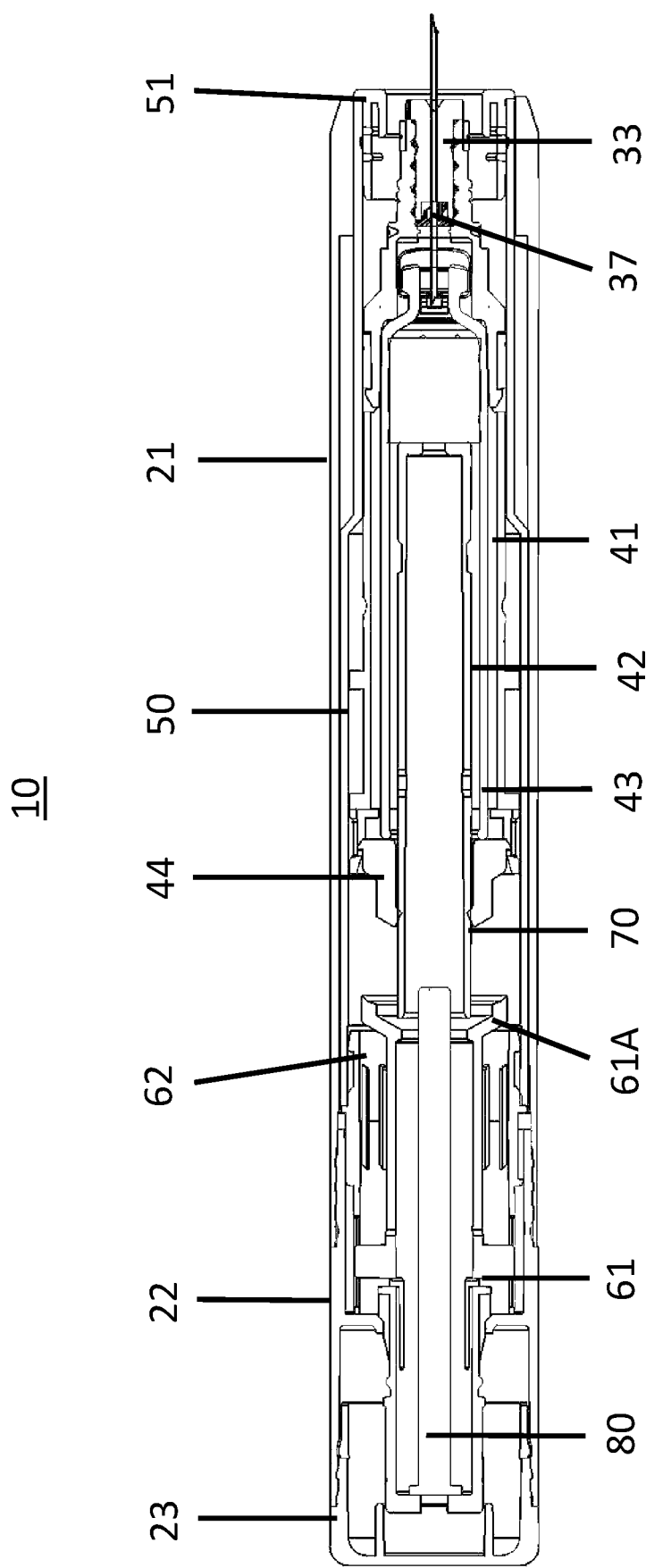
FIG. 7 is a cross-sectional view of the example autoinjector after the stopper reaches the proximal end of the medicament container's interior.

FIG. 7 is a cross-sectional view of the example autoinjector 10 after the stopper 43 reaches the proximal end of the medicament container's 42 interior. This marks the end of the medicament injection that propels the medicament through the needle 38 to enter the injection site. At this moment, the needle cover 50 is still pressed against the injection site which forces the needle cover 50 to be kept in the confine of the front shell 21. Further, the second sleeve 62 is coupled with the distal end of the needle cover 50 and thus is moved in the distal direction together with the needle cover 50 as long as it is pressed against the injection site. In addition, there is a second resilient member (not illustrated) between the second sleeve 62 and the rear shell 22 that applies forces on the second sleeve 62 in the proximal direction. As the needle cover 50 is pressed against the injection site, the second sleeve 62 is moved in the distal direction which forces the second resilient member to compress and absorb the forces from the needle cover 50.

Figure 8:
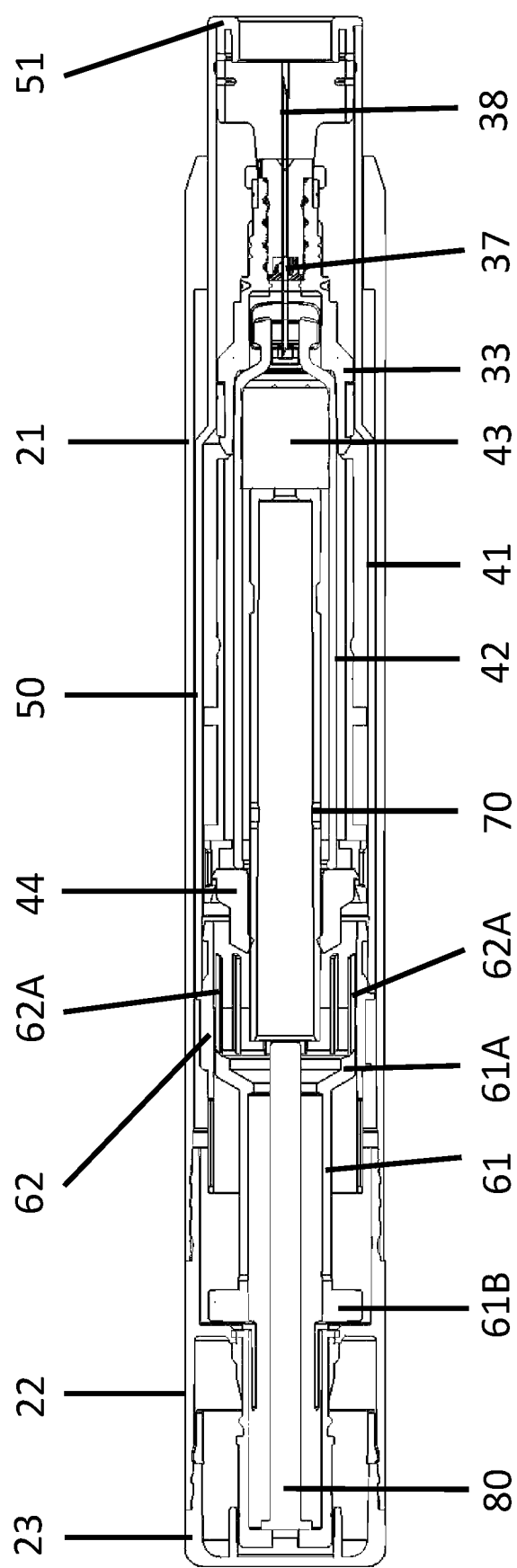
FIG. 8 is a cross-sectional view of the example autoinjector removed from the injection site after medicament injection is complete.

FIG. 8 is a cross-sectional view of the example autoinjector 10 taken away from the injector site. When the needle cover 50 is no longer pressed against the injection site, there is also no more forces compressing the second resilient member (not illustrated) disposed between the second sleeve 62 and the rear shell 22. Thus, the second resilient member decompresses to push the second sleeve 62 and the associated needle cover 50 in the proximal direction, in order for the needle cover 50 to protrude outside the front shell 21 and cover the needle 38. At the same time, the first resilient member can no longer moves the plunger rod 70 in the proximal direction. However, the first resilient member can still exert forces to push the guide rod 80 in the distal direction which then abut the first sleeve 61 to also move in the distal direction. In the present embodiment, the first sleeve 61 has an abutment portion 61B configured to collide with the inner surface of rear shell 22 when the first sleeve 61 is moved toward the distal end of the autoinjector 10. The collision between the abutment portion 61B and the rear shell 22 will generate audio signals to tell the user that the autoinjector 10 is safely removed from the injection site.

Further, the second sleeve 62 includes a plurality of obstructions portions 62A disposed on the inner surface of the second sleeve 62. The inner space of the second sleeve 62 where the obstruction portions 62A are disposed has small diameter than the rest of the inner space. While the first sleeve 61 is moved in the distal direction, the engagement portions 61A will collide with the obstruction portions 62A and are forced to flex radially inward in order for the engagement portions 61A to pass through the inner space of the second sleeve 62 where the obstruction portions 62A are disposed. The engagement portions 61A will flex radially outward once they pass over the obstruction portions 62A. Afterward, the proximal ends of the engagement portions 61A will face directly at the distal ends of the obstruction portions 62A and are ready to engage the obstructions portions 62A to prevent the second sleeve 62 from being moved in the distal direction. As mentioned above, the distal portion of the needle cover 50 is coupled with the second sleeve 62. Thus, by engaging the second sleeve 62, the engagement portions 61A also prevent the needle cover 50 from being moved in the distal direction. Therefore, even if the needle cover 50 is pressed against an object, the needle cover 50 will not be moved in the distal direction and thus can continue to cover the needle 38 to prevent accidental needle injury.

Figure 9:
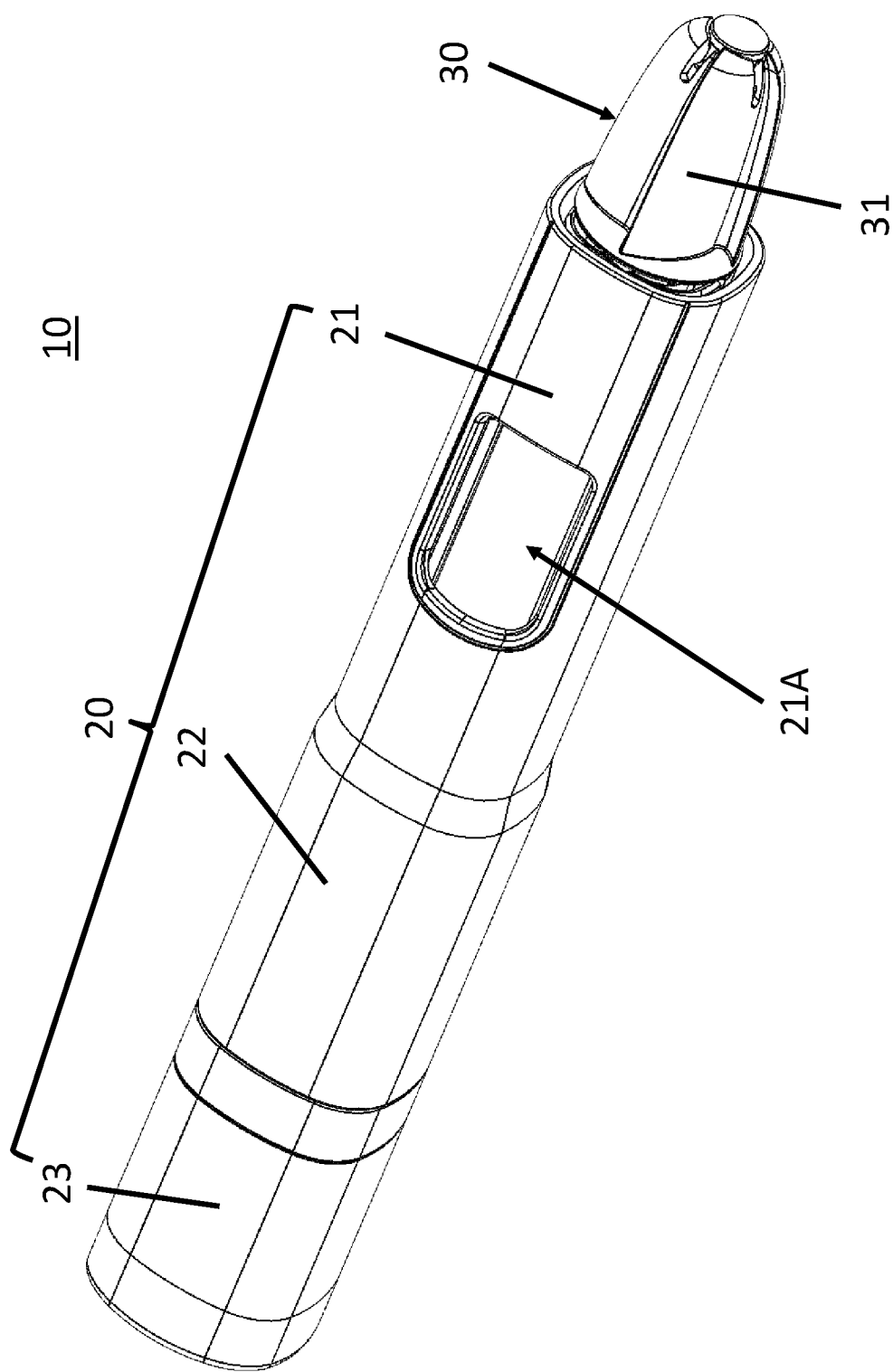
FIG. 9 is a perspective view of the example autoinjector according to a second embodiment of the present disclosure.

FIG. 9 shows a perspective view of the example autoinjector 10 according to a second embodiment of the present disclosure. As illustrated, the autoinjector 10 includes a housing 20 that further includes a front shell 21, a rear shell 22, and a rear shell cap 23 each having threads designed to allow coupling between them through rotation. However, in other embodiments, the components of the housing 20 can have other configurations known in the art such as cams and grooves that allow the manufacturers to couple them together. The autoinjector 10 further includes a needle assembly 30 according to the second embodiment substantially identical to the needle assembly 30 of the first embodiment described above. However, in the present embodiment, the outer cap 31 of the needle assembly 30 is fixedly coupled with the front shell 21. In the present embodiment, the front shell 21 and outer cap 31 each having threads designed to allow coupling between them through rotation. However, in other embodiments, the two components can have other configurations known in the art such as cams and grooves that allow the manufacturers to couple them together.

Further, as illustrated in FIG. 9, the front shell 21 includes an opening 21A through which a container carrier and a container can be seen. This allows the user to see the movement of a stopper within the container during medicament injection.

Figure 10:
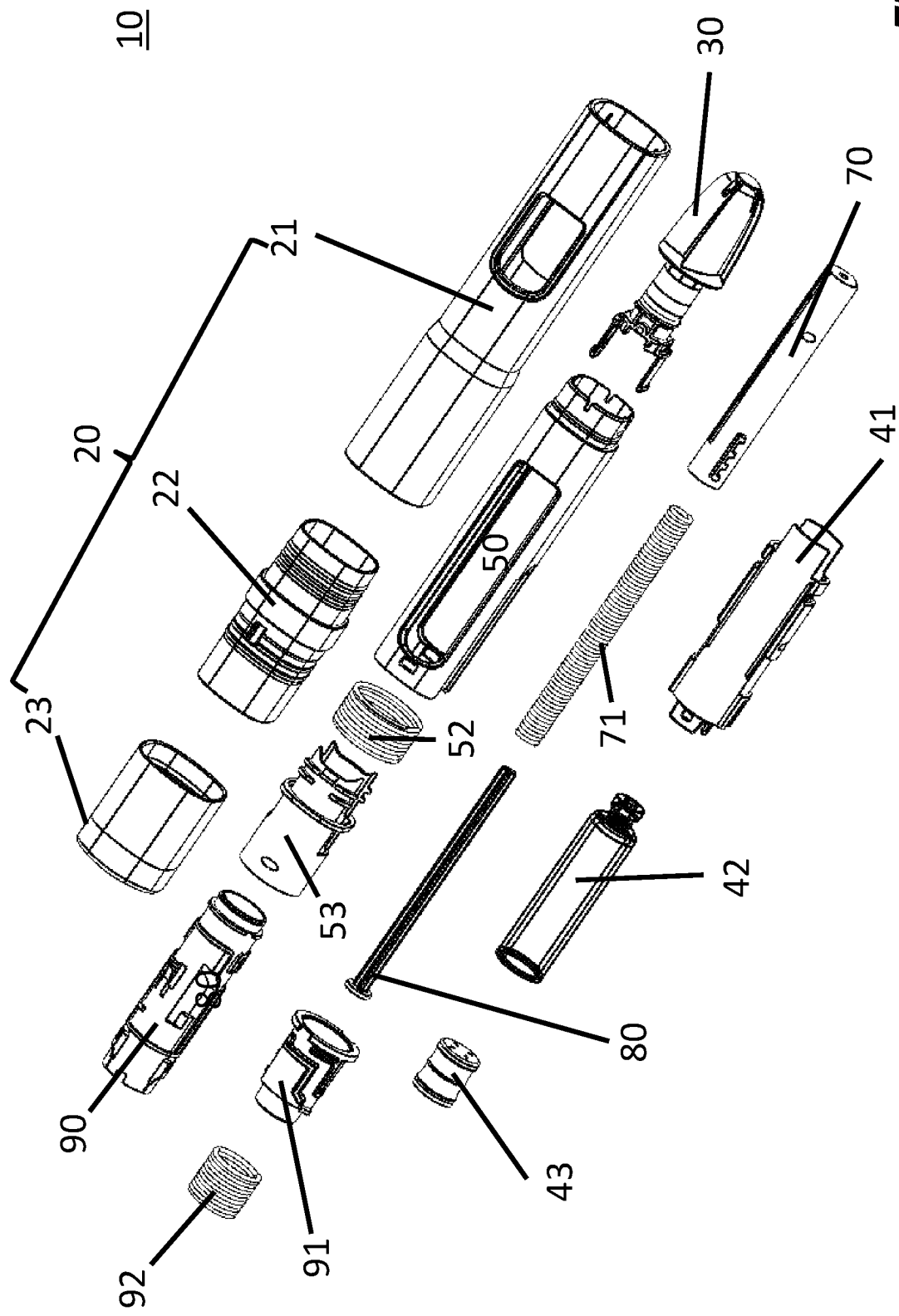
FIG. 10 is an exploded view of the example autoinjector according to a second embodiment of the present disclosure.

FIG. 10 shows an exploded view of the example autoinjector 10 according to a second embodiment of the present disclosure. As illustrated, the autoinjector 10 includes the front shell 21, a rear shell 22, a rear shell cap 23, a needle assembly 30, a container carrier 41, a medicament container 42, a stopper 43, a needle cover 50, a needle cover spring 52, a needle cover link 53, a plunger rod 70, a plunger rod spring 71, a guide rod 80, a rotator 90, a rotator carrier 91, and a plunger spring 92. The outer housing comprising the front shell 21, rear shell 22, and rear shell cap 23 are configured to accommodate the majority of the needle assembly 30 (except for the outer cap 31) and the rest of the components mentioned above. The container carrier 41 is configured to accommodate the medicament container 42 and the stopper 43 for sealing the distal end of the medicament container 42. Also, the container carrier 41 and medicament container 42 will be accommodated in the needle cover 50 and are preferably made of transparent material, so that user can see the movement of the stopper 43 through the openings on the front shell 21 and the needle cover 50.

As mentioned above, the needle assembly 30 illustrated in FIG. 10 is substantially identical to the needle assembly 30 of the first embodiment described above. Thus, the components included in the needle assembly 30 and the interaction between them will not be further described.

The needle cover link 53 is coupled with the distal end of the needle cover 50. The needle cover spring 52 is located between the rear shell 22 and the needle cover link 53. The distal end of the needle cover spring 52 is in contact with a protrusion on the inner surface of the rear shell 22. On the other hand, the proximal end of the needle cover spring 52 is in contact with a protrusion on the outer surface of the needle cover link 53. The result is that the needle cover spring 52 applies a force in the distal direction on the rear shell 22 and a force in the proximal direction on the needle cover link 53. In the present embodiment, the assembly of the needle cover 50 and the needle cover link 53 is movable relative to the rear shell 22. Thus, the needle cover spring 52 will constantly try to decompress and move the needle cover 50 and needle cover link 53 in the proximal direction. However, the outer cap 21 coupled to the front shell 21 will abut the needle cover 50 and prevent its movement in the proximal direction. Therefore, until the outer cap 21 is removed, the entire needle cover 50 will be contained inside the housing 20.

Also, the rotator carrier 91 is coupled with the distal portion of the rotator 90 while the plunger spring 92 is placed on the distal end of the rotator carrier 91. In the present embodiment, the rotator 90 and the rotator carrier 91 are rotatably coupled. In other words, the rotator 90 and rotator carrier 91 are not rotatable relative to each other.

FIGS. 11A-B are perspective view of the example autoinjector 10 according to a second embodiment before the outer cap 31 is removed. In FIG. 11B, the rear shell cap 23 and plunger spring 92 are removed while the front shell 21 and rear shell 22 are made transparent to facilitate illustration. As discussed above, the needle cover spring 52 (not illustrated) constantly applies a force on the needle cover 50 and needle cover link 53 (transparent) in the proximal direction. However, the outer cap 21 coupled with the front shell 21 prevents the needle cover 50 and needle cover link 53 from being moved in the proximal direction. Here please also refer to FIG. 17A for the interaction between needle cover link 53, and rotator 90; FIG. 18A for the interaction between the rear shell 22 and rotator carrier 91; FIG. 19A for the interaction between plunger rod 70 and rotator 90. These interactions will be further explained below.

Figure 17A:
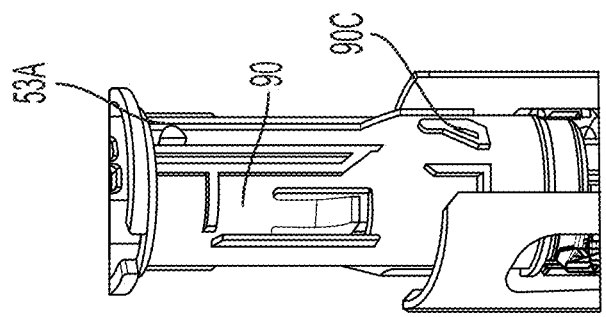
FIGS. 17A, 17B, 17C, 17D and 17E are perspective views of the rotator interacting with a first protrusion on the inner surface of the needle cover link.

FIG. 17A is a perspective view of the rotator 90 interacting with a first protrusion 53A on the inner surface of the needle cover link 53 (not illustrated). As illustrated, the first protrusion 53A is located in a trough between two protrusions on the outer surface of the rotator 90. At this moment, the outer cap 31 has not been removed and the needle cover spring 52 is prevented from moving the needle cover 50 and needle cover link 53 in the proximal direction. Thus, the first protrusion 53A remains in the distal end of the trough.

FIG. 18A is a perspective view of the rotator carrier 91 interacting with a second protrusion 22A on the inner surface of the rear shell 22 (not illustrated). As illustrated, the rotator carrier 91 includes a first blocking member 91A on the outer surface, wherein the first blocking member 91A has a first section 91B, second section 91C, and third section 91D for interacting with the second protrusion 22A. In the present embodiment, the plunger spring 92 (not illustrated) is disposed on the distal end of the rotator carrier 91 and constantly applies a force on the rotator carrier 91 in the proximal direction indicated by the arrow A. However, because of the engagement between the second protrusion 22A and first section 91B, the second protrusion 22A is able to prevent the rotator carrier 91 from being moved in the proximal direction.

FIG. 19A is a perspective view of the plunger rod 70 interacting with the inner surface of the rotator 90. In the present embodiment, the plunger rod 70 includes a third protrusion 70A on its outer surface while the plunger rod spring 71 (not illustrated) applies a force on the plunger rod 70 in the proximal direction indicated by arrow A. On the other hand, the rotator 90 includes a second blocking member 90A and a third blocking member 90B for interacting with the third protrusion 70A. As illustrated, the third protrusion 70A under the forces of plunger rod spring 71 engages the distal end of the second blocking member 90A which prevents the plunger rod 70 from being moved in the proximal direction.

Figure 12A:
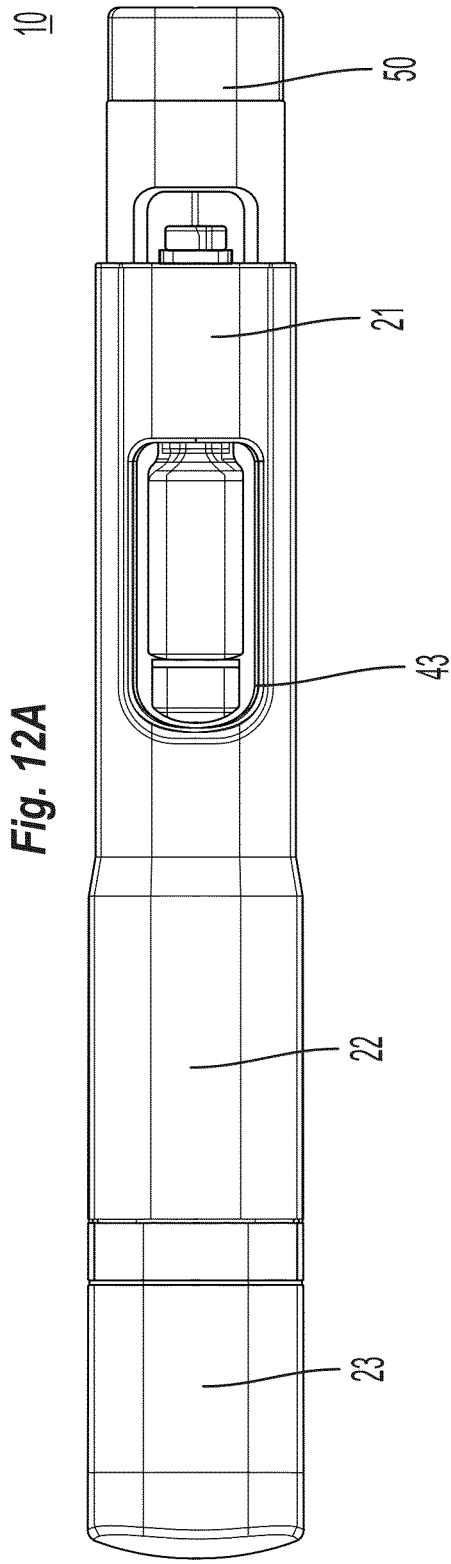
FIGS. 12A and 12B are perspective views of the example autoinjector according to a second embodiment after the outer cap 31 is removed.
Figure 12B:
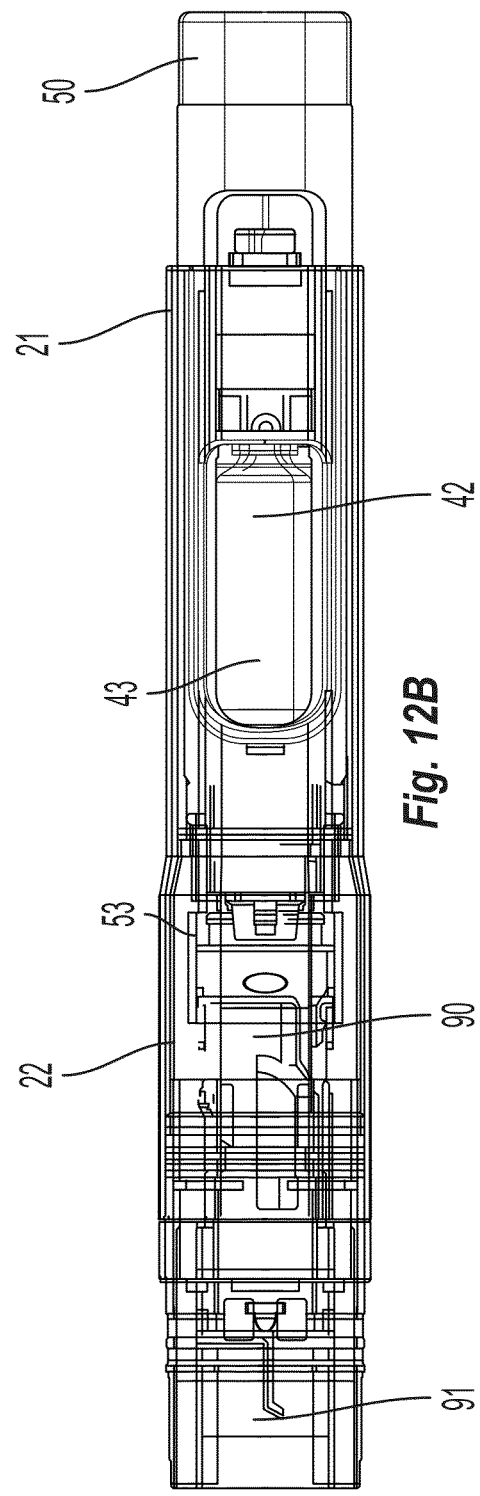

FIG. 12A-B are perspective view of the example autoinjector 10 according to a second embodiment after the outer cap 31 is removed. As mentioned above, the removed outer cap 31 was coupled with the front shell 21 to prevent the needle cover spring 52 from moving the needle cover 50 and needle cover link 53 in the proximal direction. Thus, after the outer cap 31 is removed, the needle cover spring 52 is now able to move the needle cover 50 and needle cover link 53 in the proximal direction, until a flange on the outer surface of needle cover link 53 abuts and engages protrusions disposed on the inner surface of front shell 21. The engagement between said flange and protrusions prevents the needle cover 50 and needle cover link 53 from being moved further in the proximal direction by the needle cover spring 52.

Figure 17B:
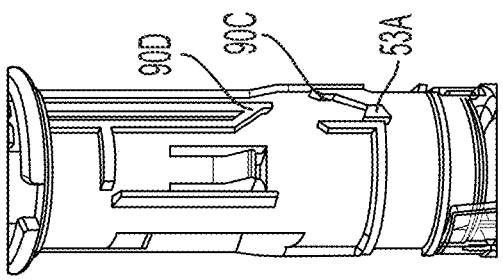

FIG. 17B is a perspective view of the rotator carrier 91 interacting with the first protrusion 22A after the outer cap 31 is removed. As mentioned above, the needle cover spring 52 moves the needle cover 50 and needle cover link 53 in the proximal direction. The first protrusion 53A of needle cover link 53 is also moved in the proximal direction to interaction with a fourth blocking member 90C on the outer surface of rotator 90. More specifically, the first protrusion 53A will interact with a slant of the fourth blocking member 90C and continues to move until the needle cover link 53 is blocked by the front shell 21 as discussed above. Here please note that as the first protrusion 53A moves along the slant of the fourth blocking member 90C, it also rotates the rotator 90 in an anti-clockwise direction looking from the distal end of the autoinjector 10.

Figure 18C:
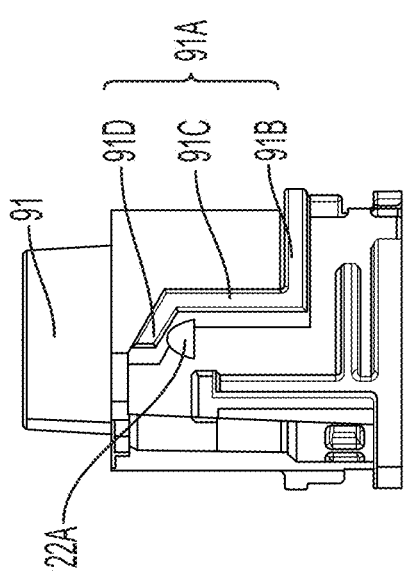
FIGS. 18A, 18B, 18C and 18D are perspective views of the rotator carrier interacting with a second protrusion on the inner surface of the rear shell.
Figure 18D:
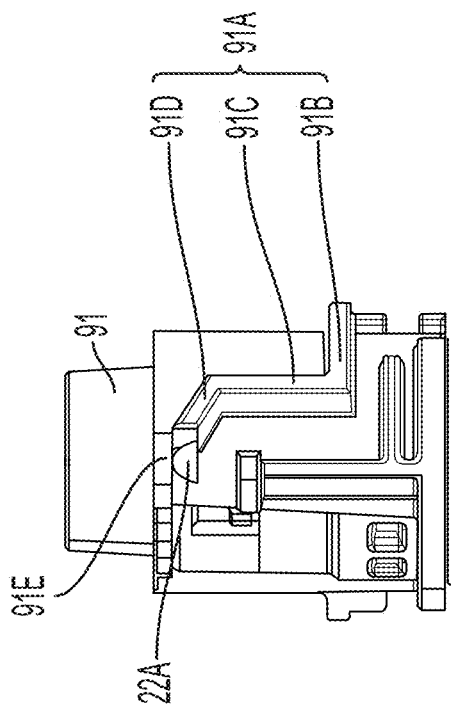
Figure 18A:
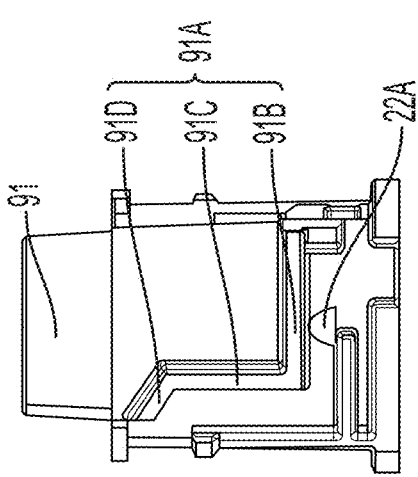
Figure 18B:
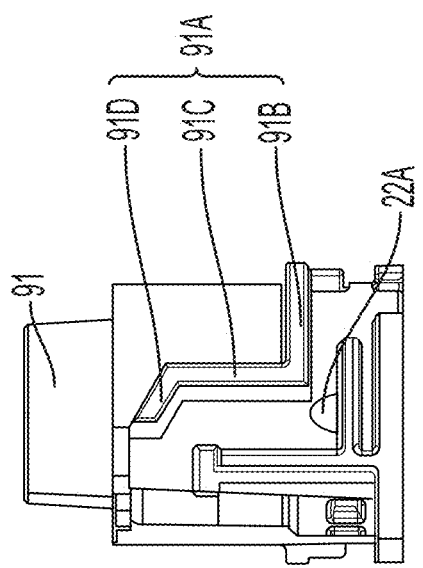

FIG. 18B is a perspective view of the rotator carrier 91 interacting with the first protrusion 22A after the outer cap 31 is removed. As mentioned above, the interaction between the first protrusion 53A and fourth blocking member 90C of rotator 90 results in the rotation of the rotator 90. Also, the rotator 90 and rotator carrier 91 are rotatably coupled. Thus, the rotator carrier 91 is also rotated in an anti-clockwise direction looking from the distal end of the autoinjector 10. The result is that the second protrusion 22A moves over the first section 91B to a position where there is a space between the second protrusion 22A and the third section 91D.

FIG. 19B is a perspective view of the plunger rod 70 interacting with the inner surface of the rotator 90, after the outer cap 31 is removed. As mentioned above, the interaction between the first protrusion 53A and fourth blocking member 90C of rotator 90 results in the rotation of the rotator 90. The result is that the third protrusion 70A moves over the distal end of the second blocking member 90A to create a space for the plunger rod spring 71 to move the plunger rod 70 in the proximal direction. The plunger rod 70 then will apply forces on the stopper 43 which in turn applies forces on the medicament inside the medicament container 42 to get any air out through a needle 38 attached to the medicament container 42, until the third protrusion 70A abuts the second blocking member 90A again, as illustrated in FIG. 19B.

Figure 13A:
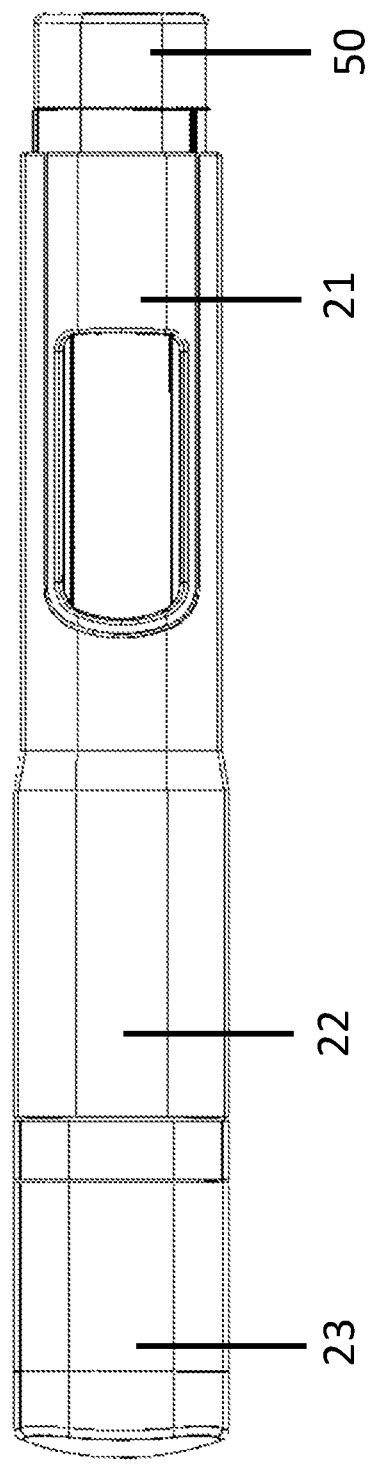
FIGS. 13A and 13B are perspective views of the example autoinjector according to a second embodiment after the needle cover is pressed against an injection site.
Figure 13B:
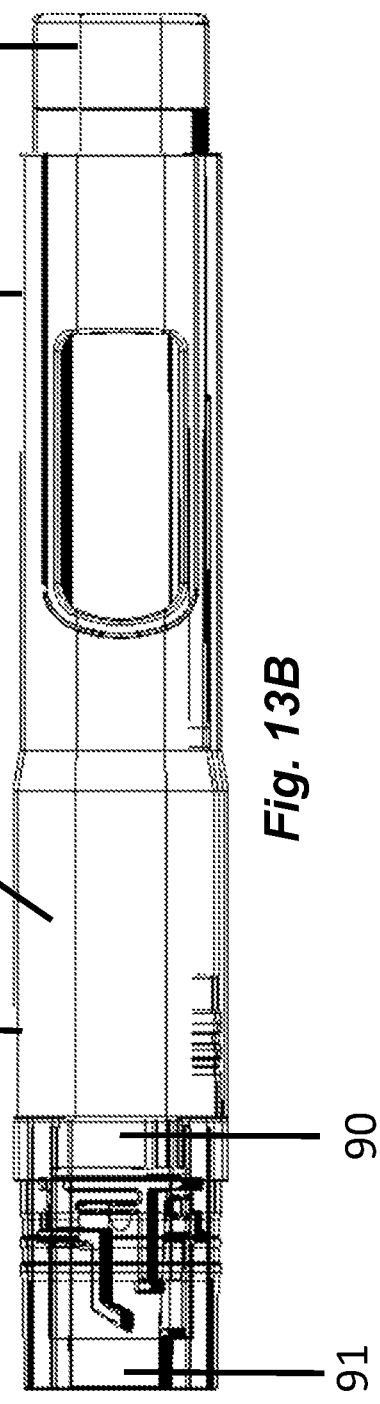
Figure 17C:
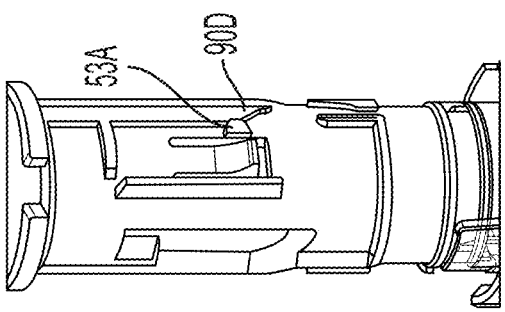

FIG. 13A-B are perspective view of the example autoinjector 10 according to a second embodiment after the needle cover 50 is pressed against an injection site. As illustrated in FIGS. 13A-B, the needle cover 50 and the associated needle cover link 53 are moved in the distal direction. Here please refer to FIG. 17C illustrating the interaction between the first protrusion 53A and the rotator 90. As the needle cover link 53 is moved in the distal direction, its first protrusion 22A eventually will interact with a slant on a fifth blocking member 90D. The first protrusion 22A will travel over said slant and rotates the rotator 90 again in the anti-clockwise direction. Here please refer to FIG. 19C illustrating the interaction between the plunger rod 70 and the rotator 90. As the rotator 90 is rotated again by the first protrusion 53A of the needle cover link 53, the third protrusion 70A is now facing a groove located between the second blocking member 90A and third blocking member 90B. This allows the plunger rod spring 71 to apply forces on the plunger rod 70 to move it in the proximal direction. The result is that the forces is transferred from the plunger rod 70 to the stopper 43 and then to the medicament in the medicament container 42. However, because the medicament is basically incompressible, the plunger rod 70 instead will move the assembly of the container carrier 41, medicament container 42, and stopper 43 in the proximal direction. Also, the proximal end of rotator 90 is coupled with the distal end of container carrier 41. Thus, the rotator 90 and rotator carrier 91 are also moved in the proximal direction.

Figure 14A:
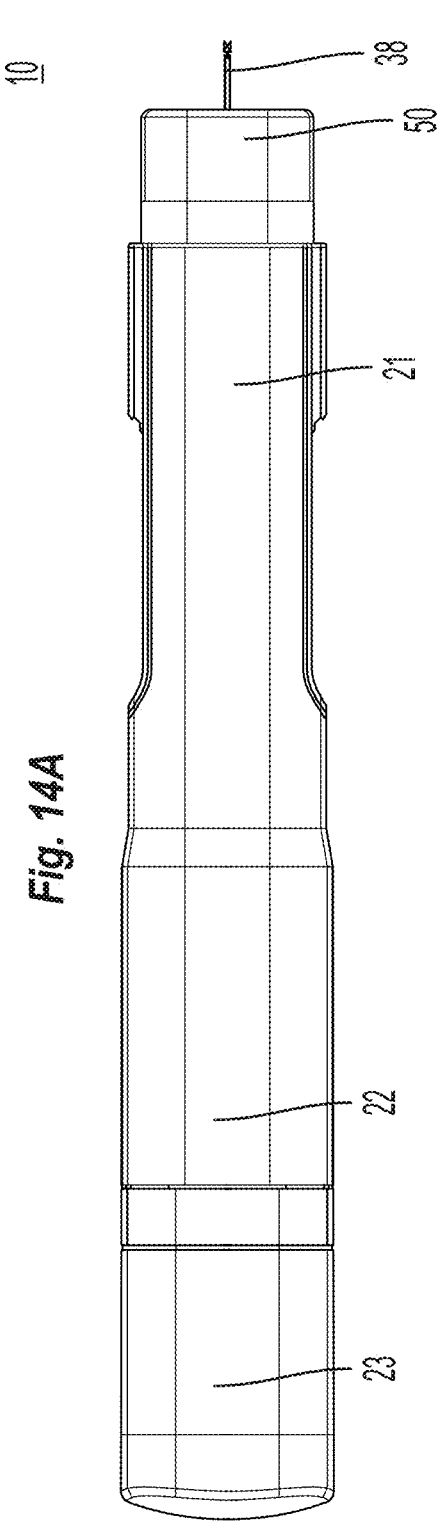
FIGS. 14A and 14B are perspective views of the example autoinjector according to a second embodiment at the end of needle penetration.
Figure 14B:
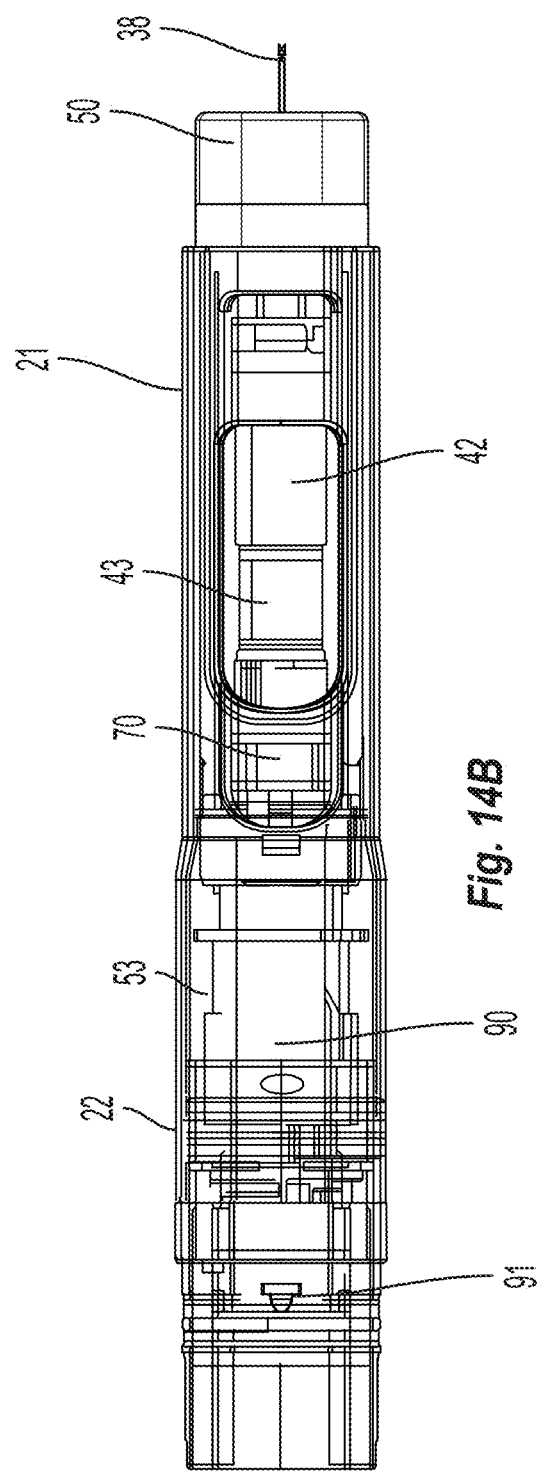

FIGS. 14A-B are perspective view of the example autoinjector 10 according to a second embodiment after the plunger rod spring 70 is released to apply forces on the plunger rod 70 in the proximal direction. As illustrated, the needle 38 attached to the medicament container 42 protrudes outside the needle cover 50 to penetrate the injection site. Also, at this moment, the container carrier 41 abuts and engages the inner surface of the needle cover 50. Thus, the assembly of the container carrier 41, medicament container 42, stopper 43, the rotator 90, and rotator carrier 91 can no longer be moved in the proximal direction by the plunger rod spring 70. This marks the end of the needle penetration and the beginning of medicament injection. At this moment, the forces applied on the stopper 43 can no longer move said assembly of the container carrier 41, medicament container 42, stopper 43, the rotator 90, and rotator carrier 91 in the proximal direction. Instead, the forces will push the stopper 43 in the proximal direction to push the medicament out of the medicament container 42 through its needle 38 and into the injection site. The medicament injection ends when the stopper 43 reaches the proximal end of the medicament container's interior space, as illustrated in FIG. 15B.

Here please refer to FIGS. 18C-D for illustration. As the rotator 90 and rotator carrier 91 are moved in the proximal direction (illustrated in FIG. 13B), the second protrusion 22A eventually will abut the third section 91D of the first blocking member 91A. In the present embodiment, the third section 91D is a slant structure and therefore the second protrusion 22A will abut the third section 91D, rotator the rotator carrier 91, and is eventually stopped by a fourth section 91E as illustrated in FIG. 18D.

Figure 17D:
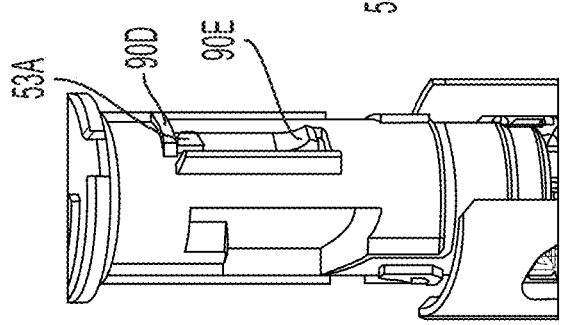

As discussed above, the rotator carrier 91 is rotated by the second protrusion 22A, when moved in the proximal direction. The rotator 90 is rotatably coupled with the rotator carrier 91. Thus, as the first protrusion 53A of needle cover 50 is moved in the distal direction, it will abut the fifth member 90D again. At the same time, the rotation of rotator 90 will bring the first protrusion 53A to the position illustrated in FIG. 17D. Here please refer to FIG. 19C for illustration. As the rotator 90 and rotator carrier 91 are rotated by the second protrusion 22A, the third protrusion 70A will be aligned with a groove between the second and third blocking members 90A, 90B. At this moment, the groove allows the plunger rod spring 71 to push the plunger rod 70 and move the stopper 43 in the proximal direction to force the medicament out of the needle 38. However, the medicament is relatively incompressible. Instead, the assembly of the container carrier 41, medicament container 42, stopper 43, the rotator 90, and rotator carrier 91 is moved in the proximal direction, until the container carrier 41 abuts and engages the inner surface of the needle cover 50 and marks the end of needle penetration into the injection site. Then, the plunger rod spring 71 continues to move the plunger rod 70 in the proximal direction to push the medicament out through the needle 38, until the third protrusion 70A abuts the second blocking member 90A again, as illustrated in FIG. 19D. This marks the end of the medicament injection into the injection site.

Figure 17E:
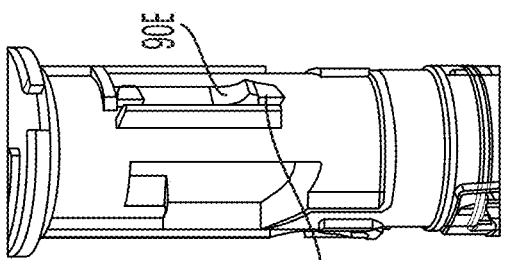

FIGS. 16A-B are perspective view of the example autoinjector 10 according to a second embodiment after the autoinjector 10 is removed from the injection site. As the needle cover 50 is removed from the injection site, the needle cover spring 52 will push the needle cover 50 and needle cover link 53 in the proximal direction, so that the needle cover 50 can cover the needle 38 to prevent accidental needle injury. Here please refer to FIGS. 17D-E for illustration. In the present embodiment, the sixth blocking member 90E is a radially flexible arm with its end portion protruding radially outward. Thus, as the needle cover link 53 is moved in the proximal direction by the needle cover spring 52, its first protrusion 53A will press the sixth blocking member 90E radially inward so that it can pass the end portion of the sixth blocking member 90E to reach the position illustrated in FIG. 17E. At this moment, the end portion of the sixth blocking member 90E will block the first protrusion 53A and prevent it from being moved in the distal direction. By extension, the needle cover 50 and needle cover link 53 are also prevented from being moved in the distal direction by the sixth blocking member 90E. Accordingly, the user will not be able to move the needle cover 50 in the distal direction to expose the needle 38. In other words, accidental needle injury is prevented.

In the Figures, various engagement features for are shown for providing an engagement between one or more components of the drug delivery device. The engagement features may be any suitable connecting mechanism such as a snap lock, a snap fit, form fit, a bayonet, lure lock, threads or combination of these designs. Other designs are possible as well.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. A medicament delivery device, comprising;
a housing having a proximal end and a distal end;
a movable container assembly disposed in the housing and including a medicament container having an interior containing a medicament, wherein the medicament container comprises a stopper and a first seal sealing the interior;
a needle assembly connected to the movable container assembly comprising:
a needle;
an outer cap comprising a plurality of teeth;
an inner cap; and
a clutch positioned between the outer cap and the inner cap and configured to rotatably engage the inner cap, wherein the outer cap is configured to be manually manipulated, wherein manually manipulating the outer cap causes the plurality of teeth to engage the clutch and the clutch to rotatably engage the inner cap to move the needle toward the medicament container in order for a distal end of the needle to pierce the first seal and enter the interior;
a driver assembly disposed at a distal end of the medicament container and configured to be released and move the movable container assembly and the needle assembly toward the proximal end of the housing to an insertion position where a proximal end of the needle exits the housing; and
an activator disposed in the housing and configured to engage the driver assembly, the activator being movable from a first activator position to a second activator position where the activator releases the driver assembly to move the container assembly and the needle assembly,
wherein the driver assembly includes:
a plunger rod configured to interact with the stopper in the medicament container;
a first sleeve having at least one engagement portion configured to engage the plunger rod and prevent the plunger rod from moving;
a second sleeve configured to engage the engagement portion and prevent the engagement portion from moving and disengaging the plunger rod; and
a second resilient member configured to engage the plunger rod and applying forces on the plunger rod in a proximal direction,
wherein the activator in the second activator position moves the second sleeve to disengage the engagement portion so that the engagement portion can move and disengage the plunger rod to release the second resilient member to move the plunger rod which then engages the stopper to move the container assembly and the needle assembly toward the proximal end of the housing, and
wherein the second resilient member drives the plunger rod to push the stopper to reach a proximal end of the interior, the second resilient member then pushes the first sleeve toward the distal end of the housing to a position where the first sleeve abuts the second sleeve which abuts the activator and prevents the activator from moving toward the distal end of the housing.

2. The medicament delivery device of claim 1, further comprising a first resilient member configured to engage the activator or the driver assembly and moves the activator from the second activator position to a third activator position where the driver assembly abuts and prevents the activator from moving toward the distal end of the housing.

3. The medicament delivery device of claim 1, wherein the engagement portion is radially flexible and positioned between the second sleeve and the plunger rod, the activator moving from the first activator position to the second activator position moves the second sleeve and allows the engagement portion to flex radially outward to disengage the plunger rod.

4. The medicament delivery device of claim 1, wherein when the movable container assembly and the needle assembly are in the insertion position, the second resilient member pushes the plunger rod and the stopper to move the medicament through the distal end of the needle and then exits the needle through a proximal end of the needle.

5. The medicament delivery device of claim 1, wherein the driver assembly further includes a guide rod disposed between the second resilient member and the first sleeve, the guide rod is surrounded by the second resilient member.

6. The medicament delivery device of claim 1, wherein the needle assembly includes:
a needle holder configured to engage and hold the needle, wherein the inner cap is configured to engage and rotate the needle holder;
a retainer configured to be coupled with the movable container assembly and comprising a threaded portion threadedly engaged with the needle holder;
wherein the outer cap is configured to rotatably engage the inner cap and be manually rotated by a user to rotate the inner cap which in turn rotates the needle holder along the threaded portion and toward the medicament container in order for the distal end of the needle to pierce the first seal and enter the interior.

7. The medicament delivery device of claim 6, wherein the outer cap has a first coupler configured to couple with the inner cap so that the outer cap can remove the inner cap away from the proximal end of the medicament container when manually pulled by the user.

8. The medicament delivery device of claim 6, wherein the first seal is disposed on a proximal end of the medicament container, the needle assembly further includes a second seal positioned between the needle and the first seal, wherein the needle pierces the second seal and then the first seal when the needle holder is rotated along the threaded portion and toward the medicament container.

9. The medicament delivery device of claim 6, wherein the outer cap rotated in a first rotational direction rotates the clutch which in turn rotates the inner cap, the outer cap rotated in a second rotational direction does not engage the clutch and is prevented from rotating the clutch.

10. The medicament delivery device of claim 6, wherein the retainer has a second coupler configured to couple with the medicament container.

11. The medicament delivery device of claim 1, wherein the movable container assembly includes a container carrier configured to accommodate the medicament container, wherein the released driver assembly moves both the medicament container and the container carrier toward the proximal end of the housing to the insertion position where the housing engages the container carrier and stops a movement of the movable container assembly.

12. The medicament delivery device of claim 1, further comprising a third coupler coupling with the movable container assembly and the driver assembly, the released driver assembly moves the third coupler which in turn moves the movable container assembly and the needle assembly toward the insertion position, the driver assembly then decouples from the third coupler and then pushes the stopper to move the medicament through the distal end of the needle and then exits the needle through the proximal end of the needle.

13. A medicament delivery device, comprising:
a housing having a proximal end and a distal end;
a movable container assembly disposed in the housing and having a proximal end;
a medicament container positioned within the movable container assembly and having an interior containing a medicament, wherein the medicament container comprises a stopper and a first seal sealing the interior;
a needle assembly comprising:
 a retainer;
 a needle;
 an outer cap comprising a plurality of teeth;
 an inner cap; and
 a clutch positioned between the outer cap and the inner cap and configured to rotatably engage the inner cap,
 where the retainer is directly connected to the proximal end of the movable container assembly and where rotation of the outer cap causes the plurality of teeth to engage the clutch and the clutch to rotatably engage the inner cap causing the needle to pierce the first seal; and
a driver assembly operatively associated with the medicament container, where the driver assembly comprises:
 a hollow plunger rod containing a compressed spring that when decompressed causes the hollow plunger rod to move proximally relative to the housing and within the medicament container further causing proximal movement of both the medicament container and the movable container assembly to an insertion position where a proximal end of the needle exits the housing;
 a second compressed spring;
 a first sleeve;
 a second sleeve; and
 an activator disposed in the housing and configured to engage the driver assembly, wherein the second compressed spring is decompressed to push the first sleeve distally to a position where the first sleeve abuts the second sleeve which abuts the activator to prevent the activator from moving distally.

14. The medicament delivery device of claim 13 wherein needle assembly further comprises:
a needle holder that engages and holds the needle, wherein the inner cap rotates the needle holder when the outer cap is rotated;
wherein the retainer has a threaded portion threadedly engaged with the needle holder.

15. The medicament delivery device of claim 13, wherein the driver assembly further includes a guide rod located inside of the compressed spring.

16. The medicament delivery device of claim 13, wherein the needle assembly further comprises the clutch configured to rotate with the outer cap when the outer cap is rotated in a first direction and not rotate with the outer cap when the outer cap is rotated in a second direction.

17. The medicament delivery device of claim 13, wherein the driver assembly further comprises:
the first sleeve having an engagement portion comprising protrusions that extend into a groove on the hollow plunger rod to prevent the hollow plunger rod from moving proximally; and
the second sleeve that engages the engagement portion to prevent the protrusions from disengaging from the groove.

* * * * *